US007646133B2

(12) United States Patent
Degertekin

(10) Patent No.: US 7,646,133 B2
(45) Date of Patent: Jan. 12, 2010

(54) ASYMMETRIC MEMBRANE CMUT DEVICES AND FABRICATION METHODS

(75) Inventor: F. Levent Degertekin, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 934 days.

(21) Appl. No.: 11/077,841

(22) Filed: Mar. 11, 2005

(65) Prior Publication Data

US 2005/0203397 A1 Sep. 15, 2005

Related U.S. Application Data

(63) Continuation-in-part of application No. 11/068,129, filed on Feb. 28, 2005.

(60) Provisional application No. 60/552,082, filed on Mar. 11, 2004, provisional application No. 60/548,192, filed on Feb. 27, 2004.

(51) Int. Cl.
*H02N 2/00* (2006.01)
*A61B 8/00* (2006.01)
*B06B 1/06* (2006.01)
*H03K 5/01* (2006.01)

(52) U.S. Cl. ....................... 310/309; 600/447; 367/140; 327/100

(58) Field of Classification Search ................. 310/309, 310/322, 334; 600/447; 367/140; 327/100
See application file for complete search history.

(56) References Cited

U.S. PATENT DOCUMENTS 4,794,384 A 12/1988 Jackson
5,129,262 A * 7/1992 White et al. .................. 73/599
5,158,087 A 10/1992 Gatzke
5,560,362 A 10/1996 Sliwa, Jr. et al.
5,585,546 A 12/1996 Gururaja et al.
5,606,974 A 3/1997 Castellano et al.
5,677,823 A 10/1997 Smith
5,679,888 A 10/1997 Tohda et al.

(Continued)

OTHER PUBLICATIONS

Badi et al. Capacitive Micromachined Ultrasonic Lamb Wave Transducers Using Rectangular Membranes, Sep. 2003, IEEE Trnasactions on Ultrasonics, Ferroelectrics, and Frequency Control, vol. 50 No. 9. pp. 1191-2003.*

(Continued)

*Primary Examiner*—Thomas M Dougherty
(74) *Attorney, Agent, or Firm*—Troutman Sanders LLP; Ryan A. Schneider; James H. Yancey, Jr.

(57) ABSTRACT

Asymmetric membrane capacitive micromachined ultrasonic transducer ("cMUT") devices and fabrication methods are provided. In a preferred embodiment, a cMUT device according to the present invention generally comprises a membrane having asymmetric properties. The membrane can have a varied width across its length so that its ends have different widths. The asymmetric membrane can have varied flex characteristics due to its varied width dimensions. In another preferred embodiment, a cMUT device according to the present invention generally comprises an electrode element having asymmetric properties. The electrode element can have a varied width across its length so that its ends have different widths. The asymmetric electrode element can have different reception and transmission characteristics due to its varied width dimensions. In another preferred embodiment, a mass load positioned along the membrane can alter the mass distribution of the membrane. Other embodiments are also claimed and described.

26 Claims, 11 Drawing Sheets

U.S. PATENT DOCUMENTS

| | | | | |
|---|---|---|---|---|
| 6,122,338 | A | 9/2000 | Yamauchi | |
| 6,122,538 | A | 9/2000 | Sliwa, Jr. et al. | |
| 6,178,033 | B1 * | 1/2001 | Ford et al. | 359/247 |
| 6,201,900 | B1 | 3/2001 | Hossack et al. | |
| 6,246,482 | B1 | 6/2001 | Kinrot et al. | |
| 6,254,831 | B1 | 7/2001 | Barnard et al. | |
| 6,292,435 | B1 | 9/2001 | Savord et al. | |
| 6,314,057 | B1 | 11/2001 | Solomon et al. | |
| 6,320,239 | B1 | 11/2001 | Eccardt et al. | |
| 6,328,696 | B1 | 12/2001 | Fraser | |
| 6,330,057 | B1 | 12/2001 | Lederer et al. | |
| 6,338,716 | B1 | 1/2002 | Hossack et al. | |
| 6,426,582 | B1 | 7/2002 | Niederer et al. | |
| 6,441,449 | B1 | 8/2002 | Xu et al. | |
| 6,445,109 | B2 | 9/2002 | Percin et al. | |
| 6,461,299 | B1 | 10/2002 | Hossack | |
| 6,483,056 | B2 | 11/2002 | Hyman et al. | |
| 6,504,795 | B1 | 1/2003 | Niederer et al. | |
| 6,511,427 | B1 | 1/2003 | Sliwa, Jr. et al. | |
| 6,514,214 | B2 | 2/2003 | Kokate et al. | |
| 6,558,330 | B1 | 5/2003 | Ayter et al. | |
| 6,562,650 | B2 | 5/2003 | Ladabaum | |
| 6,571,445 | B2 | 6/2003 | Ladabaum | |
| 6,604,425 | B1 | 8/2003 | Hsu et al. | |
| 6,632,178 | B1 | 10/2003 | Fraser | |
| 6,639,339 | B1 | 10/2003 | Bernstein | |
| 6,659,954 | B2 | 12/2003 | Robinson | |
| 6,669,644 | B2 | 12/2003 | Miller | |
| 6,684,469 | B2 | 2/2004 | Horning et al. | |
| 6,707,351 | B2 | 3/2004 | Gorrell | |
| 6,714,484 | B2 | 3/2004 | Ladabaum et al. | |
| 6,787,970 | B2 | 9/2004 | Shim et al. | |
| 6,789,426 | B2 | 9/2004 | Yaralioglu et al. | |
| 6,831,394 | B2 | 12/2004 | Baumgartner et al. | |
| 6,853,041 | B2 | 2/2005 | Khuri-Yakub et al. | |
| 7,030,536 | B2 | 4/2006 | Smith et al. | |
| 7,166,486 | B2 | 1/2007 | Ohtaka et al. | |
| 2002/0009015 | A1 | 1/2002 | Laugharn et al. | |
| 2002/0039463 | A1 | 4/2002 | Degertekin et al. | |
| 2002/0048219 | A1 | 4/2002 | Ladabaum et al. | |
| 2002/0074553 | A1 | 6/2002 | Starikov et al. | |
| 2002/0074621 | A1 | 6/2002 | Cheng et al. | |
| 2002/0123749 | A1 | 9/2002 | Jain | |
| 2002/0135329 | A1 | 9/2002 | Neufeld et al. | |
| 2003/0029242 | A1 | 2/2003 | Yaralioglu et al. | |
| 2003/0114760 | A1 | 6/2003 | Robinson | |
| 2004/0002655 | A1 | 1/2004 | Bolorforosh et al. | |
| 2004/0075364 | A1 | 4/2004 | Mehta | |
| 2004/0085858 | A1 | 5/2004 | Khuri-Yakub et al. | |
| 2004/0113524 | A1 | 6/2004 | Baumgartner et al. | |
| 2004/0174773 | A1 | 9/2004 | Thomenius et al. | |
| 2004/0180466 | A1 | 9/2004 | Foglietti et al. | |
| 2004/0236223 | A1 | 11/2004 | Barnes et al. | |
| 2004/0267134 | A1 | 12/2004 | Hossack et al. | |
| 2005/0121734 | A1 | 6/2005 | Degertekin et al. | |
| 2005/0177045 | A1 | 8/2005 | Degertekin et al. | |
| 2005/0200241 | A1 | 9/2005 | Degertekin | |
| 2005/0200242 | A1 | 9/2005 | Degertekin | |
| 2005/0203397 | A1 | 9/2005 | Degertekin | |
| 2006/0075818 | A1 | 4/2006 | Huang et al. | |
| 2006/0116585 | A1 | 6/2006 | Nguyen-Dinh et al. | |

OTHER PUBLICATIONS

Notification of the Transmittal of International of the International Search Report and The Written Opinion of the International Search Authority, European Patent Office, Oct. 31, 2005.

PCT International Search Report and Written Opinion Concerning Application No. PCT/US05/03898 dated Dec. 27, 2006.

PCT International Search Report and Written Opinion Concerning Application No. PCT/US05/06408 dated Dec. 27, 2007.

PCT International Search Report and Written Opinion Concerning Application No. PCT/US04/037089 dated Feb. 7, 2008.

J. Knight, J. McLean, and F.L. Degertekin, *Low Temperature Fabrication of Immersion Capacitive Micromachined Ultrasonic Transducers on Silicon and Dielectric Substrates*, IEEE Transactions on UFFC, vol. 51, No. 10, pp. 1324-1333, Oct. 2004.

J. McLean and F.L. Degertekin, *Interdigital Capacitive Micromachined Ultrasonic Transducers for Sensing and Pumping in Microfluidic Applications*, Proceedings of the 12th International Conference on Solid State Sensors and Actuators, pp. 915-918, Jun. 2003.

J. Knight and F.L. Degertekin, *Fabrication and Characterization of cMUTs for Forward Looking Intravascular Imaging*, Proceedings of 2003 IEEE Ultrasonics Symposium, pp. 577-580, Oct. 2003.

N. A. Hall, R. Guldiken, J. McLean, and F.L. Degertekin, *Modeling and Design of cMuts using Higher Order Vibration Modes*, Proceedings of 2004 IEEE Ultrasonics Symposium, pp. 260-263, 2004.

J. McLean, R. Guldiken, and F.L. Degertekin, *CMUTs with Dual Electrode Structure for Improved Transmit and Receive Performance*, Proceedings of 2004 IEEE Ultrasonics Symposium, pp. 501-504, Aug. 2004.

U. Demirci, A.S. Ergun, O. Oralkan, M. Karaman, B.T. Khuri-Yakub, *Forward-Viewing CMUT Arrays for Medical Imaging*, IEEE Transactions on UFFC, vol. 51, No. 7, pp. 886-894, Jul. 2004.

J. Knight and F. L. Degertekin, *Capacitive Micromachined Ultrasonic Transducers for Forward Looking Intravascular Imaging Arrays*, Proceedings of 2002 IEEE Ultrasonics Symposium, pp. 1079-1082, 2002.

X.C. Jin, I. Ladabaum, F.L. Degertekin, S. Calmes and B.T. Khuri-Yakub, *Fabrication and Characterization of Surface Micromachined Capacitive Ultrasonic Immersion Transducers*, IEEE Journal of Microelectromechanical Systems, vol. 8, No. 1, pp. 100-114, Mar. 1999.

S. Calems, C. Cheng, F.L. Degertekin, X.C. Jin, S. Ergun and B.T. Khuri-Yakub, *Highly Integrated 2-D Capacitive Micromachined Ultrasonic Transducers*, Proceedings of 1999 IEEE Ultrasonics Symposium, pp. 1163-1166, 1999.

W. Lee, N. A. Hall, Z. Zhou, and F. L. Degertekin, *Fabrication and Characterization of a Micromachined Acoustic Sensor with Integrated Optical Readout*, IEEE Journal of Selected Topics on Quantum Electronics, vol. 10, No. 3, pp. 643-651, May/Jun. 2004.

International Search Report for PCT/US2005/06408 dated Sep. 5, 2007.

European Patent Office Communication Relating To The Results Of The Partial International Search Relating to International Patent Application No. PCT/US2005/008259, Aug. 25, 2005.

Jeff McLean and F. Levent Degertekin, *Capacitive Micromachined Ultrasonic Transducers With Asymmetric Membranes for Microfluidic Applications*, 2001 IEEE Ultrasonics Symposium, pp. 925-928 (0-7803-7177-1/01).

PCT International Search Report and Written Opinion Concerning PCT Application No. PCT/US2005/06474 Dated Oct. 16, 2006 Issued by the US Patent & Trademark Office.

* cited by examiner

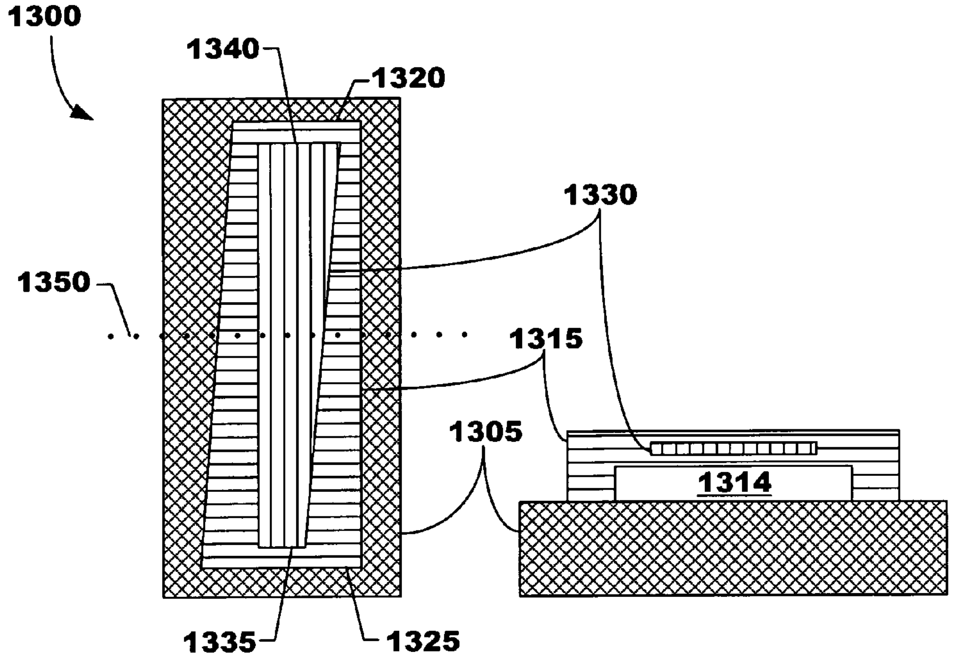
FIG. 13A FIG. 13B
FIG. 13
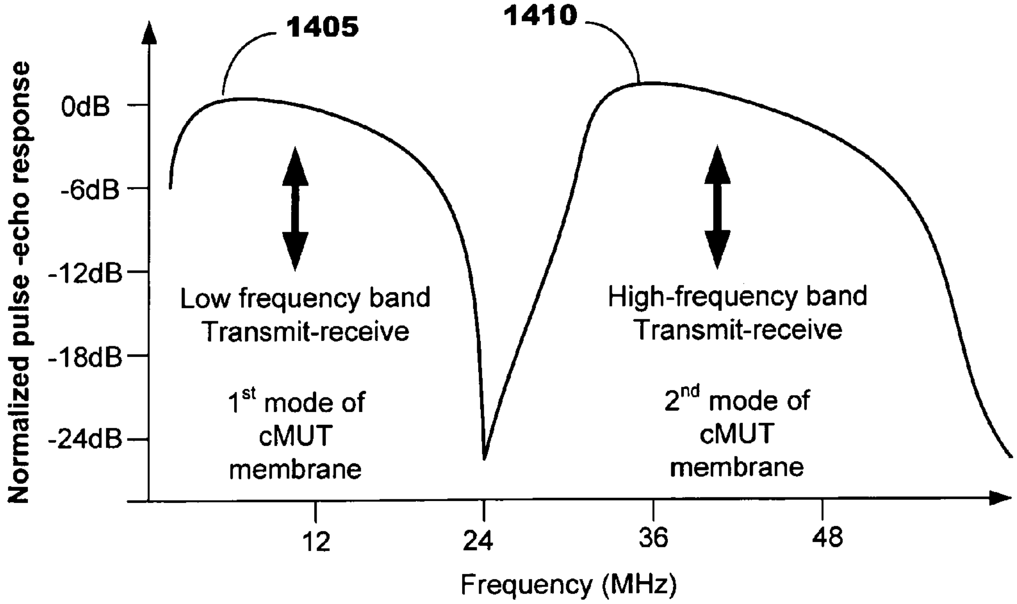
FIG. 14

FIG. 18A
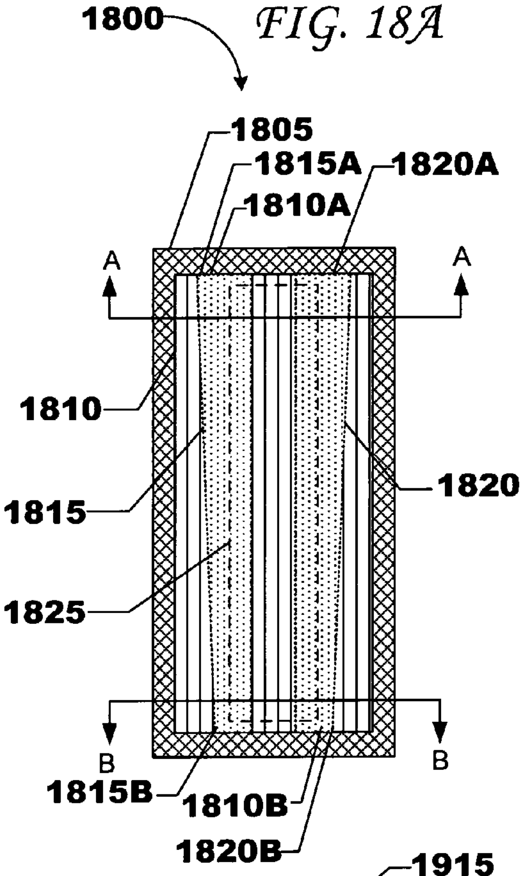
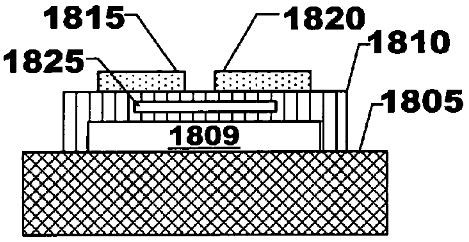
FIG. 18B
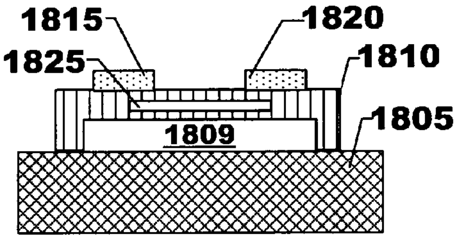
FIG. 18C
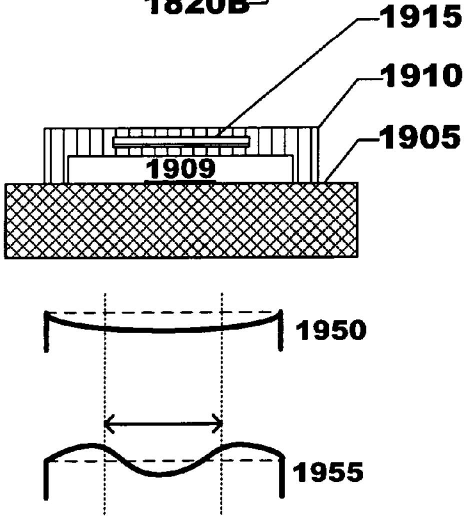
FIG. 19A
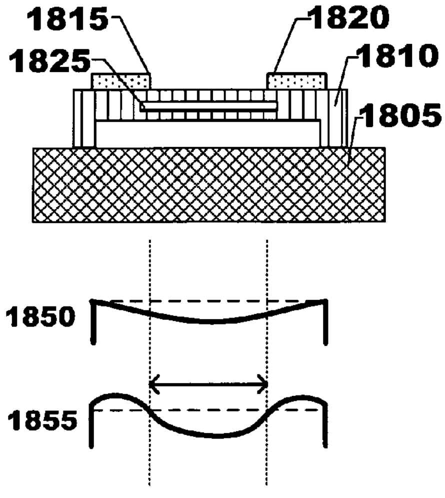
FIG. 19B

ASYMMETRIC MEMBRANE CMUT DEVICES AND FABRICATION METHODS

CROSS REFERENCE TO RELATED APPLICATIONS AND PRIORITY CLAIMS

This application claims the benefit of U.S. Provisional Application Ser. No. 60/552,082 filed on 11 Mar. 2004. This application also claims priority to and is a continuation-in-part of U.S. patent application Ser. No. 11/068,129, filed on 28 Feb. 2005, and entitled "Harmonic CMUT Devices and Fabrication Methods", which claims the benefit of U.S. Provisional Application Ser. No. 60/548,192 filed on 27 Feb. 2004.

TECHNICAL FIELD

The present invention relates generally to chip fabrication, and more particularly, to fabricating asymmetric membrane capacitive micromachined ultrasonic transducers ("cMUTs") and cMUT imaging arrays.

BACKGROUND

Capacitive micromachined ultrasonic transducers generally combine mechanical and electronic components in very small packages. The mechanical and electronic components operate together to transform mechanical energy into electrical energy and vice versa. Because cMUTs are typically very small and have both mechanical and electrical parts, they are commonly referred to as micro-electronic mechanical systems ("MEMS") devices. cMUTs, due to their miniscule size, can be used in numerous applications in many different technical fields, including medical device technology.

One application for cMUTs within the medical device field is imaging soft tissue. Tissue harmonic imaging has become important in medical ultrasound imaging, because it provides unique information about the imaged tissue. In harmonic imaging, ultrasonic energy is transmitted from an imaging array to tissue at a center frequency ($f_o$) during transmission. This ultrasonic energy interacts with the tissue in a nonlinear fashion, especially at high amplitude levels, and ultrasound energy at higher harmonics of the input frequency, such as $2f_o$, $3f_o$, $4f_o$, etc., are generated. These harmonic signals are then received by the imaging array, and an image is formed. To receive the returned signals, ultrasonic transducers in the imaging array would preferably be sensitive to receive ultra-wideband signals.

Conventional ultrasonic transducers are not capable of performing in such a manner. For example, piezoelectric transducers are not suitable for harmonic imaging applications because these transducers tend to be efficient only at a fundamental frequency ($f_o$) and its odd harmonics ($3f_o$, $5f_o$, etc.). To compensate for the odd harmonic efficiencies of piezoelectric transducers, the transducer is typically damped and several matching layers are used to create a broad band (~90% fractional bandwidth) transducer. This approach, however, requires a trade-off between sensitivity and bandwidth, since significant energy is lost due to the backing and matching layers. Additionally, conventional piezoelectric transducers and fabrication methods do not enable device manufacturers to control or adjust the vibration harmonics of conventional piezoelectric transducers.

Conventional cMUTs are also not generally configured for tissue harmonic imaging. For example, conventional cMUTs are not adapted to and do not utilize the multiple vibration modes of a cMUT membrane. Rather, conventional cMUTs, like conventional piezoelectric transducers, have a substantially uniform circular-shaped or rectangular-shaped membrane that only utilized the first vibration mode of the cMUT membrane. In addition, conventional cMUTs and fabrication methods do not provide cMUTs capable of having adjustable vibration modes or controllable vibration harmonics. Due to the design of conventional cMUT types, a 90% fractional bandwidth is usually desired to have a reasonable signal-to-noise ratio. This fractional bandwidth, however, precludes use of multiple vibration orders of a cMUT membrane for medical imaging applications. Specifically, conventional cMUT designs are not optimized to achieve higher sensitivity over a wide bandwidth or adapted to exploit multiple vibration modes of a cMUT membrane.

Therefore, there is a need in the art for a cMUT fabrication method enabling fabrication of a cMUT with an enhanced membrane to increase and enhance cMUT device performance for tissue harmonic imaging applications.

Additionally, there is a need in the art for fabricating cMUTs to utilize multiple vibration modes and multiple vibration harmonics of a membrane to increase and enhance cMUT device performance.

Additionally, there is a need in the art for a cMUT device capable of receiving and transmitting ultrasonic energy using frequencies associated with different vibration modes for a cMUT membrane.

It is to the provision of such cMUT fabrication and cMUT imaging array fabrication that the embodiments of present invention are primarily directed.

BRIEF SUMMARY OF THE INVENTION

The present invention comprises variable width membrane cMUT array transducer fabrication methods and systems. The present invention also comprises cMUTs with variable width electrode elements. The present invention provides cMUTs for imaging applications having enhanced membranes and multiple-element electrodes for optimizing the transmission and receipt of ultrasonic energy or waves, which can be especially useful in medical imaging applications. The cMUTs of the present invention can have membranes with non-uniform mass distributions adapted to receive a predetermined frequency. The present invention also provides cMUTs having membranes that can be adapted to have vibration modes that are harmonically related. In addition, the present invention provides cMUTs having membranes capable of being fabricated such that the vibration harmonics of cMUT membranes can be adjusted to correspond with operational frequencies and associated harmonics. Still yet, the present invention provides cMUTs capable of being fabricated with electrodes located near multiple vibration mode peaks of cMUT membranes when the cMUT membranes are immersed in an imaging medium.

The cMUTs can be fabricated on dielectric or transparent substrates, such as, but not limited to, silicon, quartz, or sapphire, to reduce device parasitic capacitance, thus improving electrical performance and enabling optical detection methods to be used. Additionally, cMUTs constructed according to preferred embodiments of the present invention can be used in immersion applications such as intravascular catheters and ultrasound imaging.

The present invention preferably comprises a cMUT including a membrane and a membrane frequency adjustor for adjusting a vibration mode of the membrane. The membrane frequency adjustor enables adjustment of the membrane so that at least two vibration modes of the membrane are harmonically related. The membrane frequency adjustor can comprise a membrane having a non-uniform mass distribution along at least a portion of it length. The non-uniformity in mass can be provided in a number of ways, for example by varying the thickness of the membrane, varying the density of the membrane, or for example, providing the membrane with a mass load proximate the membrane. The mass load can be a single mass source providing the mass non-uniformity along its length, or it can be a plurality of separate mass loads elements located in various places along the membrane.

The cMUT can include a mass load being an electrode element of the cMUT. The mass load preferably is Gold.

The plurality of mass load elements modifies the frequency response of the membrane. The membrane can have a plurality of vibration modes, and the membrane frequency adjustor can adapt the membrane so that the vibration modes of the membrane are harmonically related. The membrane can be adapted to vibrate at a fundamental frequency and the membrane frequency adjustor can adjust the membrane to vibrate at a frequency substantially equal to twice the fundamental frequency.

The present invention can further comprise a method of controlling vibration modes of a cMUT including the steps of providing a membrane, determining a target vibration frequency of the membrane, and altering the mass distribution of the membrane along at least a portion of the length of the membrane to induce the target vibration frequency of the membrane. In a preferred embodiment, the target vibration frequency of the membrane is substantially twice a fundamental frequency of the membrane. The step of altering the mass distribution of the membrane along at least a portion of the length of the membrane can comprise providing a membrane having a varying thickness along at least a portion of the length of the membrane, or providing a membrane having a varying density along at least a portion of the length of the membrane. Preferably, the membrane has a first vibration mode and a second vibration mode that is approximately twice the frequency of the first vibration mode, the membrane being adapted to transmit ultrasonic energy at the first vibration mode and receive ultrasonic energy at the second vibration mode.

A method of fabricating a cMUT according to a preferred embodiment of the present invention comprises the steps of providing a membrane and configuring the membrane to have a non-uniform mass distribution to receive energy at a predetermined frequency. The step of configuring the membrane to have a non-uniform mass distribution can include providing a plurality of mass loads proximate the membrane. A further step of adapting the membrane to transmit ultrasonic energy at a first vibration mode and receive ultrasonic energy at a second vibration mode, wherein the second vibration mode is approximately twice the frequency of the first vibration mode, can be provided. Additionally, the membrane can be adapted so that the vibration modes of the membrane are harmonically related, and a further step of positioning an electrode element proximate a vibration mode of the membrane can be added.

A preferred embodiment of the present invention comprises a membrane and a mass load proximate the membrane. The mass load can adapt the membrane to receive energy at a predetermined frequency. In addition, a plurality of mass loads can be disposed on the membrane so that the membrane has a non-uniform mass distribution along at least a portion of its length. The mass load can be part of, proximate, or positioned along the membrane. The mass load can be of different materials than the membrane. The membrane can be formed to have regions of different thicknesses using the mass load to distribute the mass of the membrane so that the membrane's vibration modes are harmonically related. Alternatively, a portion of the non-uniform mass distribution of the membrane can be formed by patterning the membrane to have regions of varying thickness. The harmonic cMUT can also comprise a cavity defined by the membrane, a first electrode proximate the membrane, and a second electrode proximate a substrate. The cavity can be disposed between the first electrode and second electrode. The first electrode and the second electrode can be configured to have multiple elements.

In another preferred embodiment, a method to fabricate a cMUT can comprise providing a membrane proximate a substrate and configuring the membrane to have a non-uniform mass distribution along at least a portion of its length. A method to fabricate a cMUT can also comprise providing a sacrificial layer proximate the first conductive layer, providing a first membrane layer proximate the sacrificial layer, providing a second membrane layer proximate the second conductive layer, and removing the sacrificial layer. The first and second membrane layers can form the membrane. A cMUT fabrication method can also comprise shifting the frequency and shape of a vibration mode of the membrane and adapting the membrane to operate in a receive state to receive ultrasonic energy and a transmission state to transmit ultrasonic energy.

In yet another preferred embodiment, a method to control a harmonic cMUT can comprise determining a vibration mode of the membrane and positioning one or more mass loads on the membrane to induce a membrane vibration mode corresponding to a predetermined frequency. The harmonic cMUT can have a top electrode proximate a membrane, a bottom electrode proximate a substrate, and a cavity between the membrane and the bottom electrode. A method to control a harmonic cMUT can also include positioning a first electrode element to correspond with a vibration mode of the membrane. The first electrode element can be a part of a top electrode and/or a bottom electrode. A predetermined frequency can be substantially twice a fundamental frequency of a membrane. A membrane can have a first vibration mode and a second vibration mode that is approximately twice the frequency of the first vibration mode. The membrane can be adapted to transmit ultrasonic energy at a first vibration mode and receive ultrasonic energy at a second vibration mode.

In yet another preferred embodiment, a cMUT can comprise a membrane having a first end, and a second end, and the membrane can be substantially asymmetric about a lateral line of bisection. A lateral line of bisection can demarcate a position halfway between the ends of the membrane. The ends of the membrane can have different widths, and the width of the membrane at one end is preferably greater than the width of the membrane at the other end. It will be clearly understood that upon review of the detailed description and figures that the "width" dimension as used herein is different from "thickness." A membrane can embody a first collapse force, a characteristic of the membrane that is defined as the force necessary to drive the membrane to a collapse state at a first point proximate the first end, and a second collapse, similarly defined as a characteristic of the membrane as the force necessary to drive the membrane to a collapse state at a second point proximate the second end. The first collapse force is preferably different from, and lower, than the second collapse force.

A cMUT according to the present invention can also comprise an electrode element having a first end and a second end. An electrode element can be substantially asymmetric about a lateral line of bisection. A lateral line of bisection can demarcate a position between the first and second ends of the electrode element. The first end of the electrode element can have a width less than the width of the electrode element at the second end. An electrode element can be adapted to provide perhaps different amounts of force on the membrane at a first point and a second point, such that the asymmetric electrode element can be adapted to flex the membrane at the first point and the second point a substantially equal distance toward a substrate.

A membrane is also preferably adapted to have varying flex characteristics along its length. In addition, the length of the membrane measured from the first end to the second end is preferably greater than or substantially equal to two times the width of the membrane at the first end. The membrane can also be elongated, have a predetermined shape, and be adapted to transmit and receive ultra-wideband signals. In a preferred embodiment of the present invention, the membrane is substantially trapezoidal.

In still yet another preferred embodiment of the invention, a method to fabricate a cMUT generally comprises providing a membrane, and configuring the membrane to be substantially asymmetric about a lateral line of bisection. A method to fabricate a cMUT can also include configuring a membrane to have a first width at a first end of the membrane and a second width at the second end of the membrane. The first width at the first end can be greater than the second width at the second end. The membrane can also be configured to have a first flex characteristic at a first point and a second flex characteristic at a second point. The membrane can also be configured such that a distance between a first end and a second end of the membrane is greater than or substantially equal to two times the width of the membrane measured at the second end between a first side and a second side. The membrane can additionally be configured to both transmit and receive ultra-wideband signals, and into a trapezoidal shape.

A method to fabricate a cMUT can also include providing an electrode element. The electrode element can be substantially asymmetric about a lateral line of bisection. In addition, the electrode element can be configured to have a first width at a first end of the electrode element and a second width at the second end of the electrode element. The first width at the first end can be less than the second width at the second end. A method to fabricate a cMUT can also include configuring an electrode element to provide a force on a membrane at a first point and a second point and to flex the membrane at the first point and the second point a substantially equal distance toward a substrate.

These and other features as well as advantages, which characterize the various preferred embodiments of present invention, will be apparent from a reading of the following detailed description and a review of the associated drawings.

BRIEF DESCRIPTION OF THE DRAWINGS

FIG. 13A illustrates a top view of a cMUT having asymmetric properties in accordance with a preferred embodiment of the present invention.

FIG. 13B illustrates a cross-section view of a cMUT having asymmetric properties in accordance with a preferred embodiment of the present invention.

FIG. 14 illustrates a schematic pulse-echo frequency spectrum diagram for a cMUT having asymmetric properties where several vibration modes of the transducer are used separately for ultrasonic imaging over different frequency bands.

FIG. 18A illustrates a cMUT having a membrane with an asymmetric non-uniform mass distribution in accordance with a preferred embodiment of the present invention.

FIG. 18B illustrates a cross-section view of the cMUT of FIG. 18A taken at line A-A.

FIG. 18C illustrates a cross-section view of the cMUT of FIG. 18A taken at line B-B.

FIG. 19A illustrates a cross-section view of a uniform cMUT and a sample multi-mode displacement diagram for the uniform cMUT.

FIG. 19B illustrates a cross-section view of a cMUT having asymmetric properties in accordance with the present invention and sample multi-mode displacement diagram for the cMUT having asymmetric properties.

Figure 1:
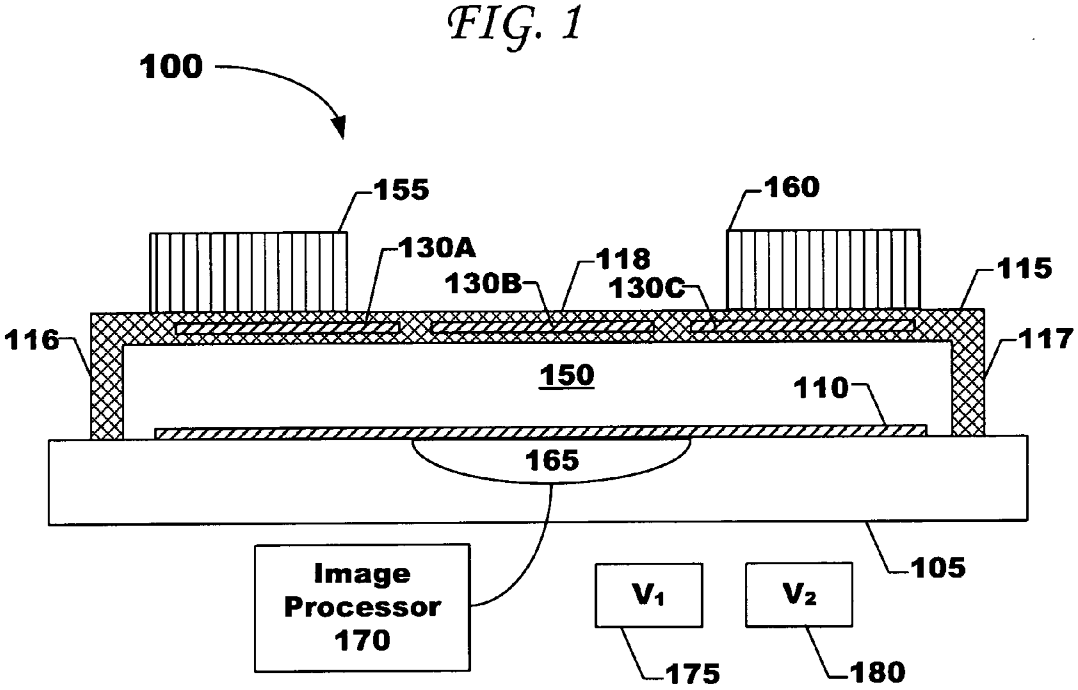
FIG. 1 illustrates a cross-sectional view of a harmonic cMUT in accordance with a preferred embodiment of the present invention.

DETAILED DESCRIPTION OF PREFERRED EMBODIMENTS cMUTs have been developed as an alternative to piezoelectric ultrasonic transducers, particularly for micro-scale and array applications. cMUTs are typically surface micromachined and can be fabricated into one or two-dimensional arrays and customized for specific applications. cMUTs can have performance comparable to piezoelectric transducers in terms of bandwidth and dynamic range, but are generally significantly smaller.

A cMUT typically incorporates a top electrode disposed within a membrane suspended above a conductive substrate or a bottom electrode proximate or coupled to a substrate. An adhesion layer or other layer can optionally be disposed between the substrate and the bottom electrode. The membrane can have elastic properties enabling it to fluctuate in response to stimuli. For example, stimuli may include, but are not limited to, external forces exerting pressure on the membrane and electrostatic forces applied through cMUT electrodes.

cMUTs are often used to transmit and receive acoustic waves. To transmit an acoustic wave, an AC signal and a large DC bias voltage are applied to a cMUT electrode disposed within a cMUT membrane. Alternatively, the voltages can be applied to the bottom electrode. The DC voltage can pull down the membrane to a position where transduction is efficient and the cMUT device response can be linearized. The AC voltage can set the membrane into motion at a desired frequency to generate an acoustic wave in a surrounding medium, such as gases or fluids. To receive an acoustic wave, a capacitance change can be measured between cMUT electrodes when an impinging acoustic wave sets a cMUT membrane into motion.

The present invention provides cMUTs comprising an enhanced membrane to control the vibration harmonics of a cMUT. A cMUT membrane according to the present invention can have a non-uniform mass distribution along the length of the membrane. The membrane can have, for example, a substantially uniform thickness, but have variations in densities providing the mass distribution profile. Alternatively, the mass distribution can be provided by varying the thickness of the membrane. If the membrane is fashioned from a single material have a substantially uniform thickness and density, mass loads can also be utilized.

Controlling the mass distribution along the membrane enables the vibration harmonics of a cMUT membrane to be controlled. As an example, multiple mass loads can be proximate, a part of, or positioned along a membrane to aid in shifting or adjusting membrane vibration modes. A cMUT membrane having a non-uniform mass distribution can enhance the transmission and reception of ultrasonic energy, such as ultrasonic waves. A cMUT membrane having a non-uniform mass distribution and a plurality of electrodes corresponding with vibration modes of a cMUT membrane can enhance the transmission and reception of ultrasonic energy, such as ultrasonic waves at desired, but separate, frequency ranges during transmission and reception. In addition, a cMUT having an enhanced membrane according to the present invention can utilize a fundamental operating frequency of a cMUT membrane and harmonic frequencies of the fundamental operating frequency to transmit and receive ultrasonic signals.

Exemplary equipment for fabricating cMUTs according to the present invention can include, but are not limited to, a PECVD system, a dry etching system, a metal sputtering system, a wet bench, and photolithography equipment. cMUTs fabricated according to the present invention generally include materials deposited and patterned on a substrate in a build-up process. The present invention can utilize low-temperature PECVD processes for depositing various silicon nitride layers at approximately 250 degrees Celsius, which is preferably the maximum process temperature when a metal sacrificial layer is used. Alternatively, the present invention according to other preferred embodiments can utilize an amorphous silicon sacrificial layer deposited as a sacrificial layer at approximately 300 degrees Celsius.

Referring now the drawings, in which like numerals represent like elements, preferred embodiments of the present invention are herein described.

FIG. 1 illustrates a cross-sectional view of a harmonic cMUT 100 in accordance with a preferred embodiment of the present invention. The cMUT 100 generally comprises various components proximate a substrate 105, including a substrate 105, a bottom electrode 110, a cavity 150, a membrane 115, and a top electrode 130 (preferably formed as a first top electrode element 130A, a second top electrode element 130B, and a third top electrode element 130C). The cMUT 100 can also comprise mass loads 155, 160, which will be understood shown exaggerated in the figures, and not to scale. The mass loads 155, 160 can be proximate, disposed on, or positioned along the membrane 115, and can be separate from, or integral with, the membrane 115. As will be discussed in further detail below with reference to FIGS. 5 and 6, a plurality of cMUTs 100 can be used in a cMUT imaging array.

The substrate 105 can be formed of silicon and can contain signal generation and reception circuits. The substrate 105 can also comprise materials enabling optical detection methods to be utilized, preferably transparent. The substrate 105 can comprise an integrated circuit 165 at least partially embedded in the substrate 105 to enable the cMUT 100 to transmit and receive ultrasonic energy or acoustical waves. In alternative embodiments the integrated circuit 165 can be located on another substrate (not shown) proximate the substrate 105.

The integrated circuit 165 can be adapted to generate and receive electrical and optical signals. The integrated circuit 165 can also be adapted to provide signals to an image processor 170. For example, the integrated circuit 165 can be coupled to the image processor 170. The integrated circuit 165 can contain both signal generation and reception circuitry or separate integrated generation and reception circuits can be utilized. The image processor 170 can be adapted to process signals received or sensed by the integrated circuit 165 and create an image from electrical and optical signals.

The bottom electrode 110 can be deposited and patterned onto the substrate 105. In an alternative embodiment, an adhesive layer (not shown) can be disposed between the substrate 105 and the bottom electrode 110. An adhesion layer can be used to sufficiently bond the bottom electrode 110 to the substrate 105. The adhesion layer can be formed of Chromium, or many other materials capable of bonding the bottom electrode 110 to the substrate 105. The bottom electrode 110 is preferably fabricated from a conductive material, such as Gold or Aluminum. The bottom electrode 110 can also be patterned into multiple, separate electrode elements (not shown), for example similar to the top electrode elements 130A, 130B, 130C. The multiple elements of the bottom electrode 110 can be isolated from each other with an isolation layer deposited on the multiple elements of the bottom electrode 110, although upon later fabrication, some of the electrode elements can be electrically coupled. An isolation layer can also be utilized to protect the bottom electrode 110 from other materials used to form the cMUT 100.

The membrane 115 preferably has elastic characteristics enabling it to fluctuate relative to the substrate 105. In a preferred embodiment, the membrane 115 comprises silicon nitride and is formed from multiple membrane layers. For example, the membrane 115 can be formed from a first membrane layer and a second membrane layer. In addition, the membrane 115 can have side areas 116, 117, and a center area 118. As shown, the center area 118 can be generally located equally between the side areas 116, 117.

The membrane 115 can also define a cavity 150. The cavity 150 can be generally disposed between the bottom electrode 110 and the membrane 115, 116, 117. The cavity 150 can be formed by removing or etching a sacrificial layer generally disposed between the bottom electrode 110 and the membrane 115. In embodiments using an isolation layer, the cavity would be generally disposed between the isolation layer and the membrane 115. The cavity 150 provides a chamber enabling the membrane 115 to fluctuate in response to stimuli, such as external pressure or electrostatic forces.

In a preferred embodiment, the multiple electrode elements 130A, 130B, 130C are disposed within the membrane 115. Alternatively, a single electrode or electrode element can be partially disposed within the membrane 115. Two or more of the multiple electrode elements 130A, 130B, 130C can be electrically coupled forming an electrode element pair. Preferably, side electrode elements 130A, 130C are formed nearer the sides 116, 117 of the membrane 115, and center electrode element 130B is formed nearer the center area 118 of the membrane 115. The electrode elements 130A, 130B, 130C can be fabricated using a conductive material, such as Gold or Aluminum. The side electrode elements 130A and 130C can be electrically coupled, and isolated from the center electrode element 130B, to form an electrode element pair. The electrode elements 130A, 130B, 130C can be formed from the same conductive material and patterned to have predetermined locations and varying geometrical configurations within the membrane 115. The side electrode element pair 130A, 130C can have a width less than the center electrode 130B, and at least a portion of the pair 130A, 130C can be placed at approximately the same distance from the substrate 105 as the center electrode element 130B. In alternative embodiments, additional electrode elements can be formed within the membrane 115 at varying distances from the substrate 105.

The electrode elements 130A, 130B, 130C can be adapted to transmit and receive ultrasonic energy, such as ultrasonic acoustical waves. The side electrode elements 130A, 130C can be provided with a first signal from a first voltage source 175 ($V_1$) and the center electrode 130B can be provided with a second signal from a second voltage source 180 ($V_2$). The side electrode elements 130A, 130C can be electrically coupled so that voltage or signal supplied to one of the electrode elements 130A, 130C will be provided to the other of the electrode elements 130A, 130C. These signals can be voltages, such as DC bias voltages and AC signals.

The side electrode elements 130A, 130C can be adapted to shape the membrane 115 to form a relatively large gap for transmitting ultrasonic waves. It is desirable to use a gap size that during transmission allows for greater transmission pressure. Further, the side electrode elements 130A, 130C can be adapted to shape the membrane 115 to form a relatively small gap for receiving ultrasonic waves. It is desirable to use a reduced gap size for reception that allows for greater sensitivity of the cMUT 100. Both the center electrode element 130B and the side electrode element elements 130A, 130C can receive and transmit ultrasonic energy, such as ultrasonic waves.

The cMUT 100 can be optimized for transmitting and receiving ultrasonic energy by altering the shape of the membrane 115. The electrode elements 130A, 130B, 130C can be provided with varying bias voltages and signals from voltage sources 175, 180 ($V_1$, $V_2$) to alter the shape of the membrane 115. Additionally, by providing the various voltages and signals, the cMUT 100 can operate in two states: a transmission state and a reception state. For example, during a receiving state, the side electrode elements 130A, 130C can be provided a DC bias voltage from the first voltage source 175 ($V_1$) to optimize the shape of the membrane 115 for receiving an acoustic ultrasonic wave.

In a preferred embodiment of the present invention, the membrane 115 has a non-uniform mass distribution along its length. The membrane 115 has a varying mass distribution across its length, which variation can be a result of one or more of the following: varying thickness, density, material composition, and other membrane characteristics along the length of the membrane.

In a preferred embodiment, mass loads 155, 160 are deposited and patterned onto the membrane 115 providing the membrane 115 with a non-uniform mass distribution. Alternatively, the membrane 115 can be patterned to have a non-uniform mass distribution such that certain points along the length of the membrane 115 have varying masses via thickness and/or density variations.

The mass loads 155, 160 are preferably formed of dense, malleable materials, including, but not limited to, Gold. Many other dense, malleable materials can be used to form the mass loads 155, 160. Gold is desirable because it is a dense, soft material, and thus does not significantly interfere with membrane vibration due to the membrane's stiffness. In a preferred embodiment of the present invention, the mass loads 155, 160 have a thickness of approximately one micro-meter and have a width of approximately two micro-meters. The size and shape of the mass loads 155, 160 can be modified to achieved desired results. The mass loads 155, 160 can be proximate the sides 116, 117, respectively. More than two mass loads 155, 160 can also be utilized in other embodiments. The mass loads 155, 160 can be used to control or adjust the vibrations and fluctuations of the membrane 115. For example, the mass loads 155, 160 can be placed or positioned to correspond with peak vibration regions of a particular vibration mode of the membrane 115.

The membrane 115, due to its elastic characteristics, can vibrate at various frequencies and can also have multiple vibration modes. For example, the membrane 115 can have a first order vibration mode as well as other higher order vibration modes (e.g., second order, third order, etc.). Adjusting the vibration modes of the membrane 115 can result in improved cMUT 100 performance. For example, shifting the vibration modes of the membrane 115 to occur at the operational frequencies and harmonics of the operational frequencies utilized by the cMUT 100 enables the membrane 115 to resonate at these frequencies when used, resulting in efficient transmission and reception of ultrasonic energy. With a combination of signals applied to and received from the voltage sources 175, 180, the transmission of ultrasonic energy can be minimized at a predetermined frequency and the received signals can be maximized at that particular frequency. Modifying the mass distribution of the membrane 115 can aid in shifting vibration modes of the membrane 115 to desired locations in the frequency spectrum for the cMUT 100. For example, the membrane 115 can be mass loaded such that it receives a predetermined frequency. The predetermined frequency can be a harmonic frequency, such as a first harmonic frequency, of a signal transmitted by the cMUT 100.

Figure 2:
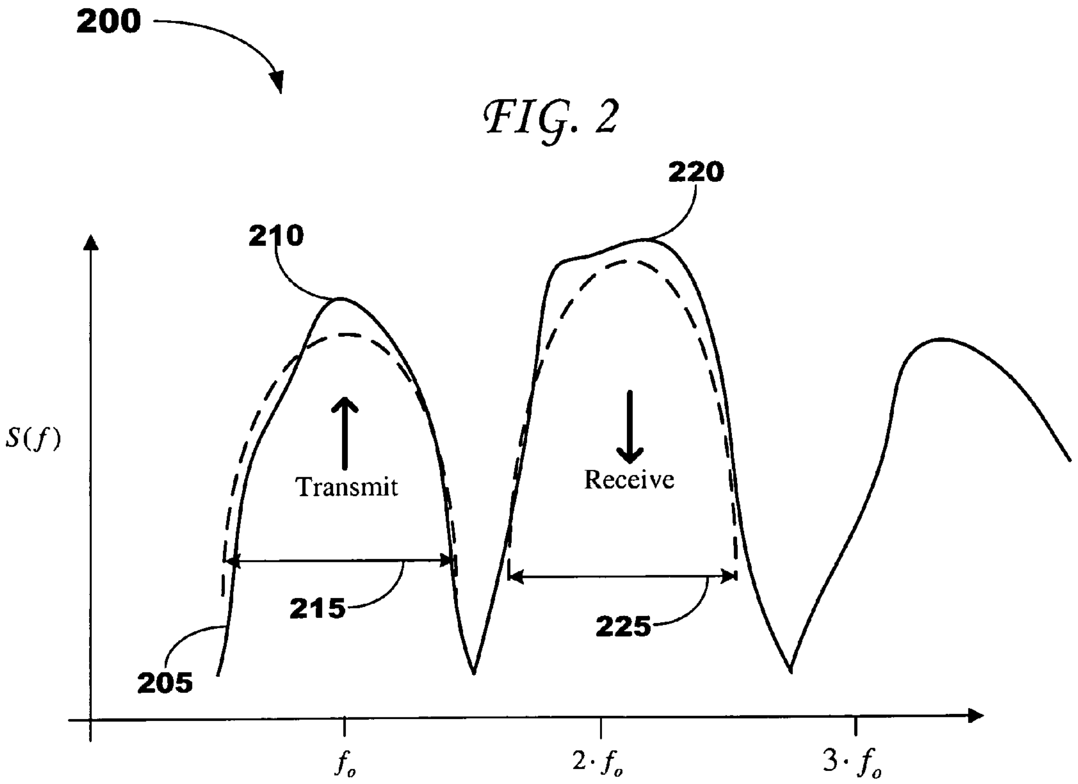
FIG. 2 illustrates a sample pulse-echo frequency spectrum of a harmonic cMUT in accordance with a preferred embodiment of the present invention.

FIG. 2 illustrates a sample pulse-echo frequency spectrum of a harmonic cMUT 100 in accordance with a preferred embodiment of the present invention. As shown, a frequency response 205 for the harmonic cMUT 100 has a first peak 210 and a second peak 220. The first peak 210 can coincide with a transmit frequency range 215 substantially centered around an operational frequency ($f_o$). The second peak 220 can coincide with a receive frequency range 225 substantially centered around a second harmonic frequency of the operational frequency ($2*f_o$). The membrane 115 of the cMUT 100 can be adjusted so that the frequency of the first vibration order is centered around the operational frequency ($f_o$) and the second vibration order is centered around the second harmonic frequency of the operational frequency ($2*f_o$). Such a configuration enables the vibration modes of the membrane 115 to be harmonically related such that the peaks of the vibration modes correspond to the operational frequency and harmonics of the operational frequency.

The membrane 115 of the cMUT 100 can be enhanced to have a frequency response as shown in FIG. 2. The membrane can be adapted to transmit and receive ultrasonic energy at a desired operational frequency and the second harmonic of the operational frequency. The present invention can also be used to enhance a cMUT membrane to operate at multiple vibration modes corresponding to a cMUT membrane. For example, the membrane 115 can be fashioned by locating mass loads in certain locations on the membrane 115, to aid in moving a third vibration mode of the membrane 115. The third vibration mode of the membrane 115 can be moved or adjusted to correspond with a third harmonic frequency ($3*f_o$) to improve transmitted and received signals at the third harmonic frequency range. In addition to shifting vibration modes to correspond with certain harmonic frequencies, broad bandwiths can be created around the harmonic frequencies by shifting the vibration modes, thus increasing the transmitted and receiving ranges of the membrane 115.

Figure 3:
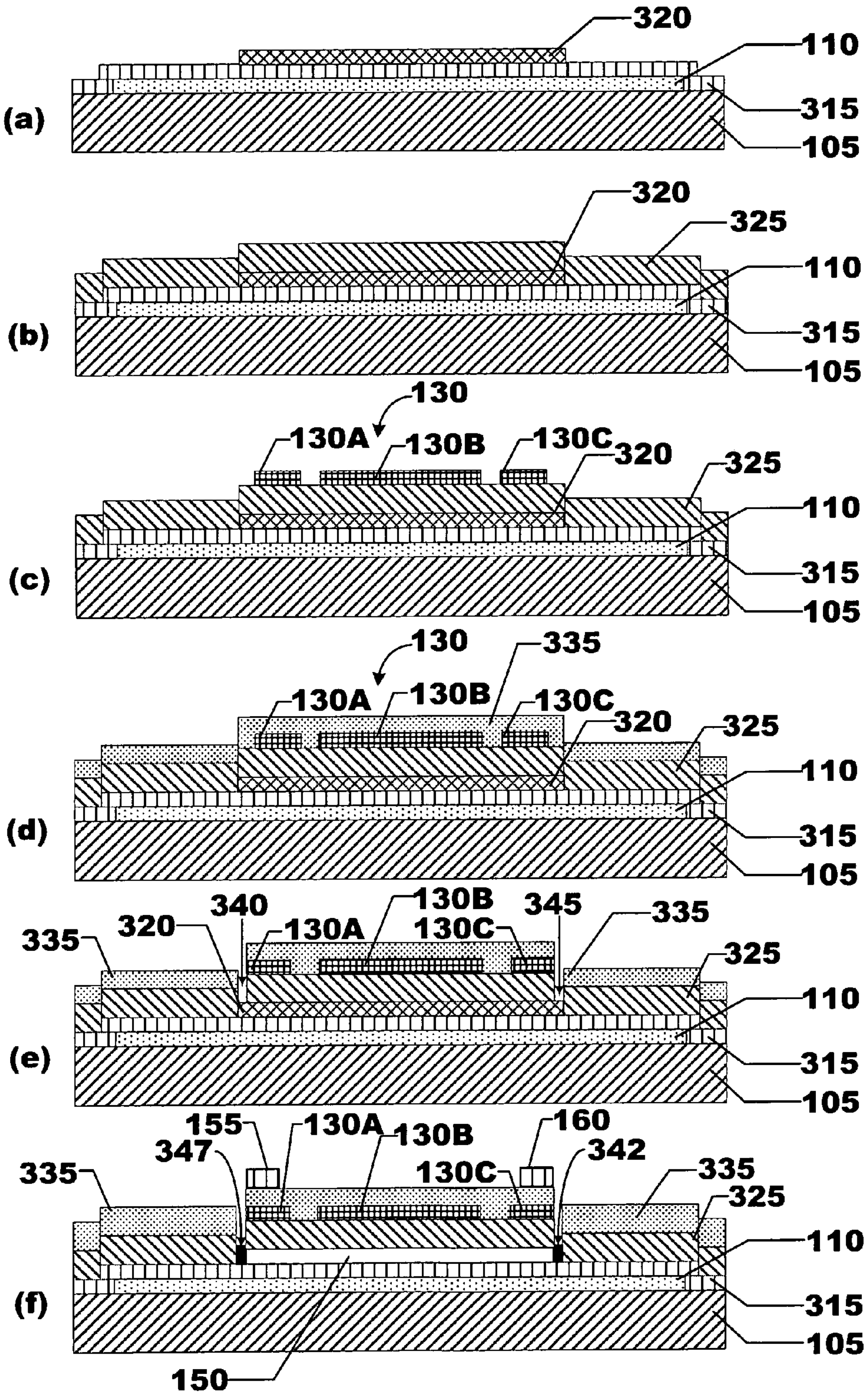
FIG. 3 illustrates a fabrication process utilized to fabricate a harmonic cMUT in accordance with a preferred embodiment of the present invention.

FIG. 3 illustrates a fabrication process utilized to fabricate a harmonic cMUT in accordance with a preferred embodiment of the present invention. Typically, the fabrication process is a build-up process that involves depositing various layers of materials on a substrate, and patterning the various layers in predetermined configurations to fabricate a cMUT 100 on the substrate 105.

In a preferred embodiment of the present invention, a photoresist such as Shipley S-1813 is used to lithographically define various layers of a cMUT. Such a photoresist material does not require the use of the conventional high temperatures for patterning vias and material layers. Alternatively, many other photoresist or lithographic materials can be used.

A first step in the present fabrication process provides a bottom electrode 110 on a substrate 105. The substrate 105 can comprise dielectric materials, such as silicon, quartz, glass, or sapphire. In some embodiments, the substrate 105 contains integrated electronics, and the integrated electronics can be separated for transmitting and receiving signals. Alternatively, a second substrate (not shown) located proximate the substrate 105 containing suitable signal transmission and detection electronics can be used. A conductive material, such as conductive metals, can form the bottom electrode 110. The bottom electrode 110 can also be formed by doping a silicon substrate 105 or by depositing and patterning a conductive material layer, such as metal, on the substrate 105. Yet, with a doped silicon bottom electrode 110, all non-moving parts of a top electrode can increase parasitic capacitance, thus degrading device performance and prohibiting optical detection techniques for most of the optical spectrum.

To overcome these disadvantages, a patterned bottom electrode 110 can be used. As shown in FIG. 3(*a*), the bottom electrode 110 can be patterned to have a different length than the substrate 105. By patterning the bottom electrode 110, device parasitic capacitance can be significantly reduced.

The bottom electrode 110 can be patterned into multiple electrode elements, and the multiple electrode elements can be located at varying distances from the substrate 105. Aluminum, chromium, and gold are exemplary metals that can be used to form the bottom electrode 110. In one preferred embodiment of the present invention, the bottom electrode 110 has a thickness of approximately 1500 Angstroms, and after deposition, can be patterned as a diffraction grading, or to have various lengths.

In a next step, an isolation layer 315 is deposited. The isolation layer 315 can isolate portions of or the entire bottom electrode 110 from other layers placed on the bottom electrode 110. The isolation layer 315 can be silicon nitride, and preferably has a thickness of approximately 1500 Angstroms. A Unaxis 790 PECVD system can be used to deposit the isolation layer 315 at approximately 250 degrees Celsius in accordance with a preferred embodiment. The isolation layer 315 can aid in protecting the bottom electrode 110 or the substrate 105 from etchants used during cMUT fabrication. Once deposited onto the bottom electrode layer 110, the isolation layer 315 can be patterned to a predetermined thickness. In an alternative preferred embodiment, an isolation layer 315 is not utilized.

After the isolation layer 315 is deposited, a sacrificial layer 320 is deposited onto the isolation layer 315. The sacrificial layer 320 is preferably only a temporary layer, and is etched away during fabrication to form a cavity 150 in the cMUT 100. When an isolation layer 315 is not used, the sacrificial layer 320 can be deposited directly on the bottom electrode 110. The sacrificial layer 320 is used to hold a space while additional layers are deposited during cMUT fabrication. The sacrificial layer 320 can be formed with amorphous silicon that can be deposited using a Unaxis 790 PECVD system at approximately 300 degrees Celsius and patterned with a reactive ion etch ("RIE"). Sputtered metal can also be used to form the sacrificial layer 320. The sacrificial layer 320 can be patterned into different sections, various lengths, and different thicknesses to provide varying geometrical configurations for a resulting cavity or via.

A first membrane layer 325 is then deposited onto the sacrificial layer 320, as shown in FIG. 3(*b*). For example, the first membrane layer 325 can be deposited using a Unaxis 790 PECVD system. The first membrane layer 325 can be a layer of silicon nitride or amorphous silicon, and can be patterned to have a thickness of approximately 6000 Angstroms. The thickness of the first membrane layer 325 can vary depending on the particular implementation. Depositing the first membrane layer 325 over the sacrificial layer 320 aids in forming a vibrating membrane 115.

After patterning the first membrane layer 325, a second conductive layer 330 can be deposited onto the first membrane layer 325 as illustrated in FIG. 3(*c*). The second conductive layer 330 can form the top electrode(s) of a cMUT. The second conductive layer 130 can be patterned into different electrode elements 130A, 130B, 130C that can be isolated from each other. The electrodes 130A, 130B, 130C can be placed at varying distances from the substrate 105. One or more of the electrode elements 130A, 130B, 130C can be electrically coupled forming an electrode element pair. For example, the side electrode elements 130A, 130C can be coupled together, forming an electrode element pair. Preferably, the formed electrode pair 130A, 130C is isolated from the center electrode element 130B.

The electrode element pair 130A, 130C can be formed from conductive metals such as Aluminum, Chromium, Gold, or combinations thereof. In an exemplary embodiment, the electrode element pair 130A, 130C comprises Aluminum having a thickness of approximately 1200 Angstroms and Chromium having a thickness of approximately 300 Angstroms. Aluminum provides good electrical conductivity, and Chromium can aid in smoothing any oxidation formed on the Aluminum during deposition. Additionally, the electrode element pair 130A, 130C can comprise the same conductive material or a different conductive material than the first conductive layer 110.

In a next step, a second membrane layer 335 is deposited over the electrode elements 130A, 130B, 130C as illustrated in FIG. 3(*d*). The second membrane layer 335 increases the thickness of the cMUT membrane 115 at this point in fabrication (formed by the first and second membrane layers 325, 335), and can serve to protect the second conductive layer 330 from etchants used during cMUT fabrication. The second membrane layer 335 can also aid in isolating the first electrode element 130A from the second electrode element 130B. The second membrane layer can be approximately 6000 Angstroms thick. In some embodiments, the second membrane layer 335 is adjusted using deposition and patterning techniques so that the second membrane layer 335 has an optimal geometrical configuration. Preferably, once the second membrane layer 335 is adjusted according to a predetermined geometric configuration, the sacrificial layer 320 is etched away, leaving a cavity 150 as shown in FIG. 3(*f*).

The first and second membrane layers 325, 335 can form the membrane 115. The membrane 115 can fluctuate or resonate in response to stimuli, such as external pressures and electrostatic forces. In addition, the membrane 115 can have multiple vibration modes due to its elastic characteristics. The location of these vibration modes can be helpful in designing and fabricating a cMUT according to the present invention. For example, the first and second conductive layers 310, 330 can be patterned into electrodes or electrode elements proximate the vibration modes of the composite membrane. Such electrode and electrode element placement can enable efficient reception and transmission of ultrasonic energy. In addition, the location of vibration modes for the membrane 115 can be adjusted and controlled by changing the mass distribution of the membrane 115.

Figure 5:
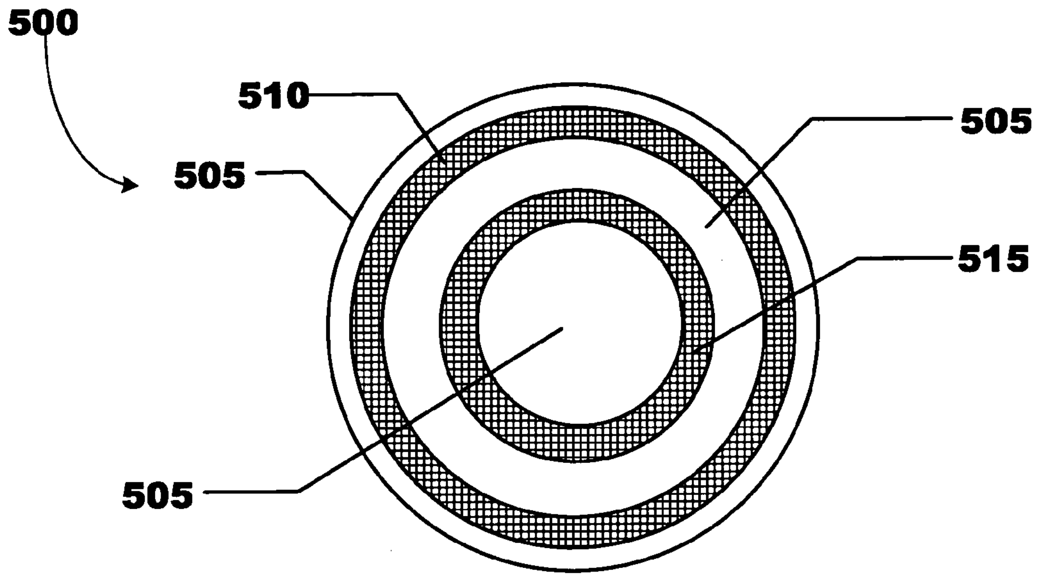
FIG. 5 illustrates a cMUT imaging array system comprising multiple harmonic cMUTs formed in a ring-annular array in accordance with a preferred embodiment of the present invention.

To enable etchants to reach the sacrificial layer 320, apertures 340, 345 can be etched through the first and second membrane layers 325, 335 using an RIE process. As shown in FIG. 3(*e*), access passages to the sacrificial layer 320 can be formed at apertures 340, 345 by etching away the first and second membrane layers 325, 335. When an amorphous silicon sacrificial layer 320 is used, one must be aware of the selectivity of the etch process to silicon. If the etching process has low selectivity, one can easily etch through the sacrificial layer 320, the isolation layer 315, and down to the substrate 105. If this occurs, the etchant can attack the substrate 305 and can destroy a cMUT device. When the bottom electrode 110 is formed from a metal that is resistant to the etchant used with the sacrificial layer, the metal layer can act as an etch retardant and protect the substrate 105. Those skilled in the art will be familiar with various etchants and capable of matching the etchants to the materials being etched. After the sacrificial layer 320 is etched, the cavity 350 can be sealed with seals 342, 347, as shown in FIG. 5(*f*).

The cavity 350 can be formed between the isolation layer 315 and the membrane layers 325, 335. The cavity 350 can also be disposed between the bottom electrode 110 and the first membrane layer 325. The cavity 350 can be formed to have a predetermined height in accordance with some preferred embodiments of the present invention. The cavity 350 enables the cMUT membrane 115, formed by the first and second membrane layers 325, 335, to fluctuate and resonate in response to stimuli. After the cavity 350 is formed by etching the sacrificial layer 320, the cavity 350 can be vacuum sealed by depositing a sealing layer (not shown) on the second membrane layer 335. Those skilled in the art will be familiar with various methods for setting a pressure in the cavity 350 and then sealing it to form a vacuum seal.

The sealing layer is typically a layer of silicon nitride, having a thickness greater than the height of the cavity 350. In an exemplary embodiment, the sealing layer has a thickness of approximately 4500 Angstroms, and the height of the cavity 350 is approximately 1500 Angstroms. In alternative embodiments, the second membrane layer 335 is sealed using a local sealing technique or sealed under predetermined pressurized conditions. Sealing the second membrane layer 335 can adapt the cMUT for immersion applications. After depositing the sealing layer, the thickness of the cMUT membrane 115 can be adjusted by etching back the sealing layer since the cMUT membrane 115 may be too thick to resonate at a desired frequency. A dry etching process, such as RIE, can be used to etch the sealing layer.

In a next step, the non-uniform mass distribution of the membrane of the cMUT can be accomplished by depositing multiple mass loads 155, 160 onto the second membrane layer 335. Multiple mass loads 155, 160 can be placed at various places on the second membrane layer 335. The location of the multiple mass loads 155, 160 on the second membrane layer 335 can correspond to vibration modes of the membrane 115 formed by the first and second membrane layers 325, 335. The multiple mass loads 155, 160 can also be used to shift or adjust the vibration modes of the membrane formed by the first and second membrane layers 325, 335 to certain predetermined areas. This feature of the present invention enables a specific vibration mode of interest to be selectively controlled. These predetermined areas can be located near the electrode elements 130A, 130B, 130C so that the electrode elements 130A, 130B, 130C can be used to transmit and receive ultrasonic acoustical waves. In an alternative embodiment, the second membrane layer 335 can be patterned to have regions of different thickness to form a membrane having a non-uniform mass distribution.

A final step in the present cMUT fabrication process prepares the cMUT for electrical connectivity. Specifically, RIE etching can be used to etch through the isolation layer 315 on the bottom electrode 110, and the second membrane layer 335 on the electrode elements 130A, 130B, 130C making them accessible for connections.

Additional bond pads can be formed and connected to the electrodes. Bond pads enable external electrical connections to be made to the top and bottom electrodes 110, 130 with wire bonding. In some embodiments, gold can be deposited and patterned on the bond pads to improve the reliability of the wire bonds.

In an alternative embodiment of the present invention, the sacrificial layer 320 can be etched after depositing the first membrane layer 325. This alternative embodiment invests little time in the cMUT 100 before performing the step of etching the sacrificial layer 320 and releasing the membrane 115 formed by the membrane layers 325, 335. Since the top electrode 130 has not yet been deposited, there is no risk that pinholes in the second membrane layer 335 could allow the top electrode 330 to be destroyed by etchants.

Figure 4:
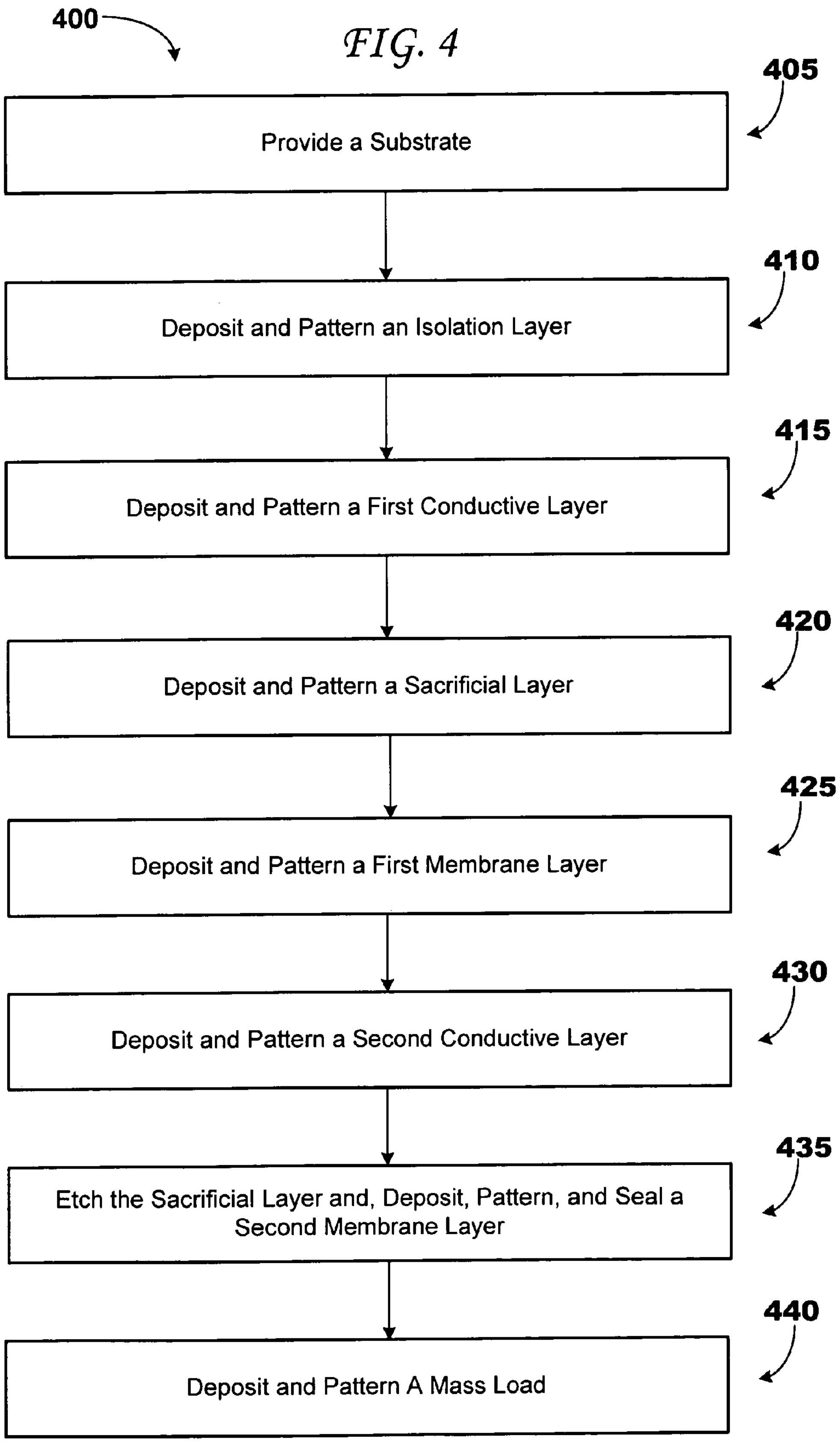
FIG. 4 illustrates a logical flow diagram depicting a fabrication process utilized to fabricate a harmonic cMUT in accordance with a preferred embodiment of the present invention.

FIG. 4 illustrates a logical flow diagram depicting a preferred method to fabricate a harmonic cMUT 100 in accordance with a preferred embodiment of the present invention. The first step involves providing a substrate 105 (405). The substrate 105 can be of various constructions, including opaque, translucent, or transparent. For example, the substrate 150 can be, but is not limited to, silicon, glass, or sapphire. Next, an isolation layer can deposited onto the substrate 105, and patterned to have a predetermined thickness (410). The isolation layer is optional, and may not be utilized in some embodiments. An adhesive layer can also be used in some embodiments ensuring that an isolation layer bonds to a substrate 105, or the bottom electrode 110 can adequately bond to the substrate 105.

After the isolation layer is patterned, a first conductive layer 110 is deposited onto the isolation layer, and patterned into a predetermined configuration (415). Alternatively, a doped surface of a substrate 105, such as a doped silicon substrate surface, can form the first conductive layer 110. The first conductive layer 110 preferably forms a bottom electrode 110 for a cMUT 100 on a substrate 105. The first conductive layer 110 can be patterned to form multiple electrode elements. At least two of the multiple electrode elements can be coupled together to form an electrode element pair.

Once the first conductive layer 110 is patterned into a predetermined configuration, a sacrificial layer 320 is deposited onto the first conductive layer 110 (420). The sacrificial layer 320 can be patterned by selective deposition and patterning techniques so that it has a predetermined thickness. Then, a first membrane layer 325 can be deposited onto the sacrificial layer 320 (425).

The deposited first membrane layer 325 is then patterned to have a predetermined thickness, and a second conductive layer 130 is then deposited onto the first membrane layer 325 (430). The second conductive layer 130 preferably forms a top electrode 130 for a cMUT 100. The second conductive layer 130 can be patterned to form multiple electrode elements 130A, 130B, 130C. At least two of the multiple electrode elements 130A, 130B, 130C can be coupled together to form an electrode element pair. After the second conductive layer 130 is patterned into a predetermined configuration, a second membrane layer 335 is deposited onto the patterned second conductive layer 130 (435). The second membrane layer 335 can also be patterned to have an optimal geometric configuration.

The first and second membrane layers 325, 335 can encapsulate the second conductive layer 130, enabling it to move relative to the first conductive layer 110 due to elastic characteristics of the first and second membrane layers 325, 335. After the second membrane layer 335 is patterned, the sacrificial layer 320 is etched away, forming a cavity 150 between the first and second conductive layers 110, 130 (435). The cavity 150 formed below the first and second membrane layers 325, 335 provides space for the resonating first and second membrane layers 325, 335 to move relative to the substrate 105. In a next step, the second membrane layer 335 is sealed by depositing a sealing layer onto the second membrane layer 335 (435).

In a final step (440), a mass load can be formed on the second membrane layer 335. Multiple mass loads can also be formed on the second membrane layer 335, and they can be placed at point on the second membrane layer 335 corresponding to vibration modes of a membrane 115 formed by the first and second membrane layers 325, 335. The mass loads are preferably formed of dense, malleable materials, such as Gold. The mass loads can aid in changing the mass distribution of the membrane layer 115 so that the membrane layer 115 has regions of varying thickness. In an alternative embodiment, the membrane layer 115 can be patterned to have regions of varying thickness or densities.

The embodiments of the present invention can also be utilized to form a cMUT array for a cMUT imaging system. Those skilled in the art will recognize that the cMUT imaging arrays illustrated in FIGS. 5 and 6 are only exemplary, and that other imaging arrays are achievable in accordance with the embodiments of the present invention.

FIG. 5 illustrates a cMUT imaging array device formed in a ring-annular array on a substrate. As shown, the device 500 includes a substrate 505 and cMUT arrays 510, 515. The substrate 505 is preferably disc-shaped, and the device 500 may be utilized as a forward looking cMUT imaging array. Although the device 500 is illustrated with two cMUT arrays 510, 515, other embodiments can have one or more cMUT arrays. If one cMUT array is utilized, it can be placed near the outer periphery of the substrate 505. If multiple cMUT arrays are utilized, they can be formed concentrically so that the circular-shaped cMUT arrays have a common center point. Some embodiments can also utilize cMUT arrays having different geometrical configurations in accordance with some embodiments of the present invention.

Figure 6:
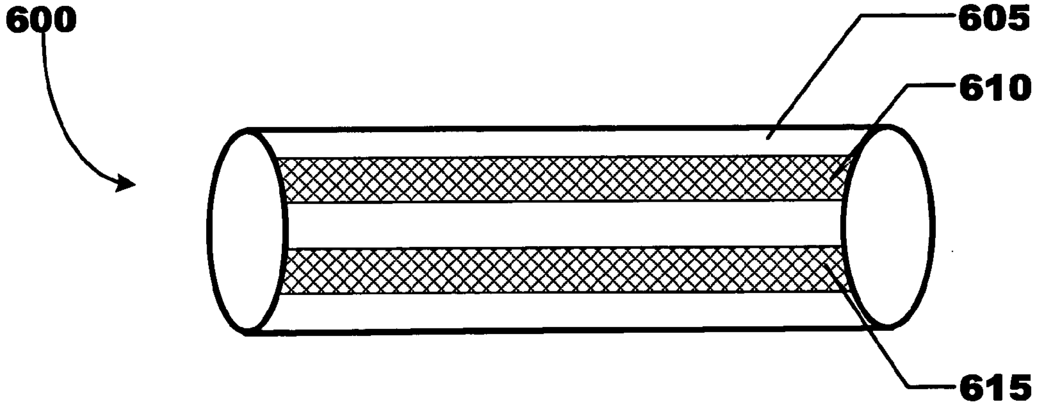
FIG. 6 illustrates a cMUT imaging array system comprising multiple harmonic cMUTs formed in a side-looking array in accordance with a preferred embodiment of the present invention.

FIG. 6 illustrates a cMUT imaging array system formed in a side-looking array on a substrate. As shown, the device 600 includes a substrate 605, and cMUT arrays 610, 615. The substrate 605 can be cylindrically-shaped, and the cMUT arrays can be coupled to the outer surface of the substrate 605. The cMUT arrays 610, 615 can comprise cMUT devices arranged in an interdigital fashion and used for a side-looking cMUT imaging array. Some embodiments of device 600 can include one or multiple cMUT imaging arrays 610, 615 in spaced apart relation on the outer surface of the cylindrically-shaped substrate 600.

The present invention also contemplates analyzing a cMUT 100 or cMUT array to determine the location of the vibration modes of a cMUT membrane and to determine the position of mass loads to adjust the vibration modes of a cMUT membrane. For convenience, the components of the cMUT discussed below are with reference to FIG. 7. The description of particular functions of the components, or specific arrangement and sizes of the components, however, are not intended to limit the scope of FIG. 7 and are provided only for example, and not limitation.

An approach to analyze a cMUT is to simulate the motion of a cMUT membrane in a fluid, such as water. For example, a finite element analysis tool, such as the ANSYS™ tool, can been used to simulate the motion of a cMUT membrane. In a preferred embodiment of the present invention, the membrane can have a width of approximately 40 μm and a thickness of approximately 0.6 μm. Alternatively, other dimensions can be used. Since the membrane can be long and rectangular, 1-D analysis can be used. Other simulations can use other dimensional analysis parameters, such as 2-D or 3-D.

Figure 7:
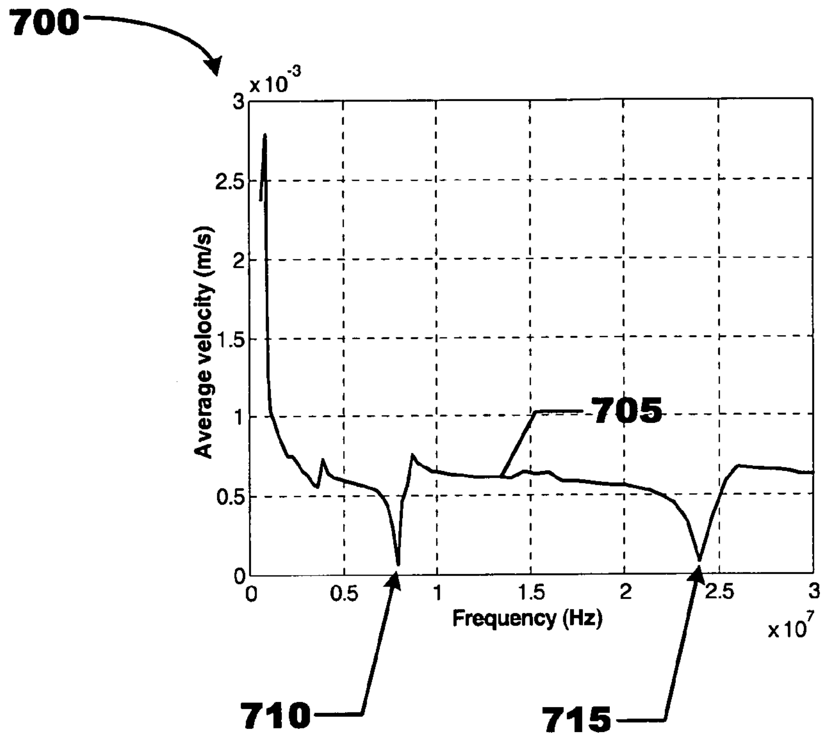
FIG. 7 is a diagram illustrating a graph illustrating the calculated average velocity as a function of frequency over the surface of the cMUTs illustrated in FIG. 7.
Figure 8:
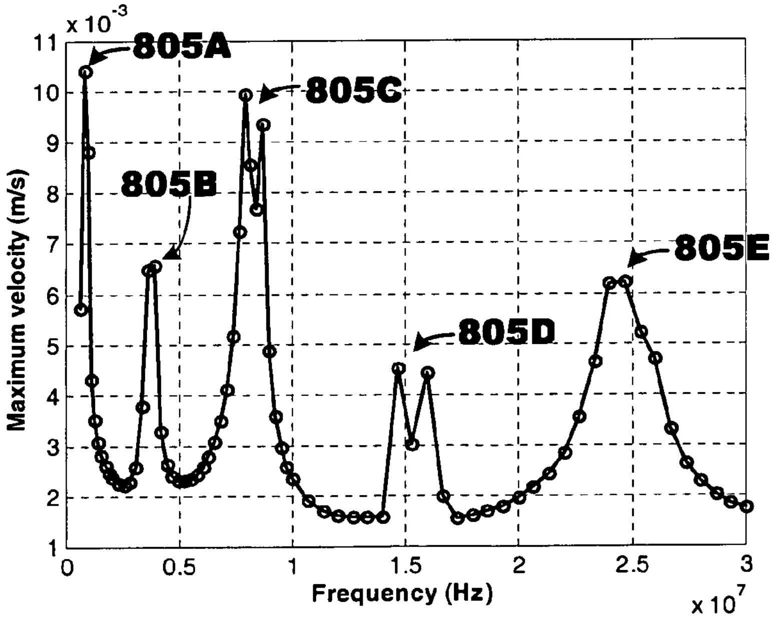
FIG. 8 is a graph illustrating the calculated peak velocity amplitude as a function of frequency over the surface of the cMUT membrane illustrated in FIG. 1.

To simulate electrostatic actuation of the cMUT a uniform pressure of 1 kPa (kilo-Pascal) can be applied to the membrane. A resulting vibration profile of the membrane can then be calculated. FIG. 7 shows an average velocity 700 over the membrane as a function of frequency. As can be seen, the spectrum 705 is relatively flat in the 2-30 MHz range with the exception of nulls 710, 715 at approximately 8 MHz and approximately 24 MHz. To further understand the vibration profile of the membrane, the maximum velocity over the membrane can be calculated and plotted, as illustrated in FIG. 8. As shown in FIG. 8, the velocity of the membrane can have five peaks 805A, 805B, 805C, 805D, 805E. The local peak velocities of the membrane can be more than an order of magnitude larger than the average velocity.

Figure 9A:
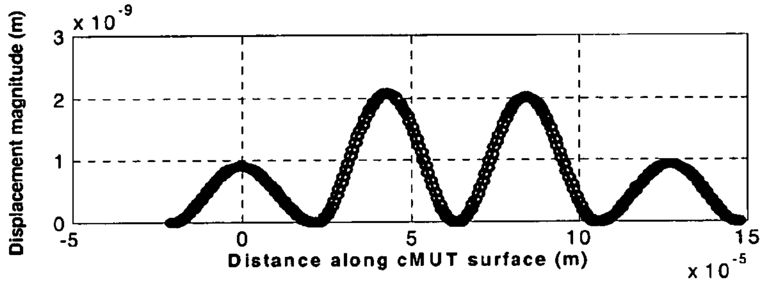
FIG. 9A is a diagram illustrating a vibration profile for the cMUT membrane illustrated in FIG. 1 at approximately 0.8 MHz.
Figure 9B:
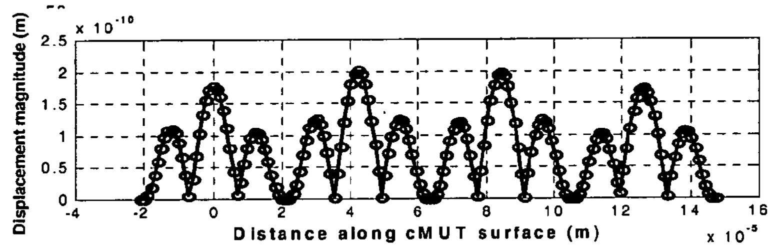
FIG. 9B is a diagram illustrating a magnitude of the vibration profile for the cMUT membrane illustrated in FIG. 1 at approximately 8 MHz
Figure 9C:
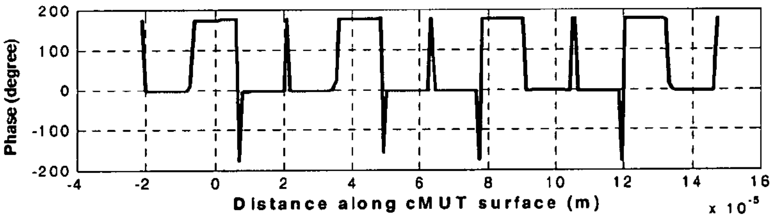
FIG. 9C is a diagram illustrating a phase of the vibration profile for the cMUT membrane illustrated in FIG. 1 at approximately at 8 MHz.

When the membrane displacement profile is plotted around the frequencies where the peaks occur, the nulls in the average velocity occur at frequencies where the membrane moves close to its third and fifth resonances. FIGS. 9A-C illustrate the vibration profiles over the membrane at 0.8 MHz and 8 MHz. These frequencies correspond to the first and third vibration modes of the membrane. Although the cMUT does not generate any considerable pressure output around 8 MHz, the membrane locally vibrates with large amplitude in response to an applied pressure. Therefore, by placing localized electrodes over the parts of the membrane where a particular mode has peak velocity, large output signals can be generated around a certain frequency range. Furthermore, by selectively displacing the location of the particular vibration mode, one can determine where the enhanced response would occur.

The present invention can also utilize the higher order vibration modes for cMUT design by selectively controlling the frequency of a particular membrane vibration mode of interest. For example, this can be accomplished by disposing mass loads on the membrane at predetermined locations. The mass distribution of a membrane can be altered by depositing and patterning mass loads on a uniform membrane, resulting in a membrane with a non-uniform mass distribution. The third vibration mode, for example, is targeted and the mass loads are concentrated on the regions of the membrane having peak strain energy (i.e. peaks).

Figure 10A:
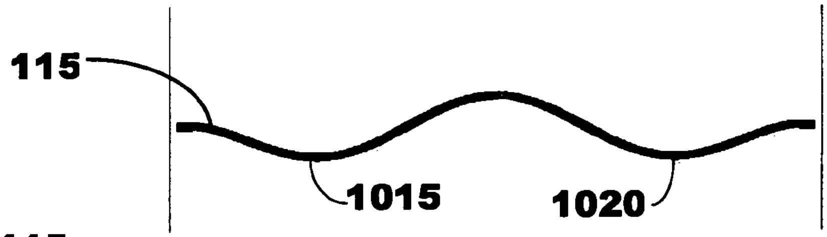
FIG. 10A is a diagram illustrating a cross section of a cMUT membrane vibrating at its third mode.
Figure 10B:
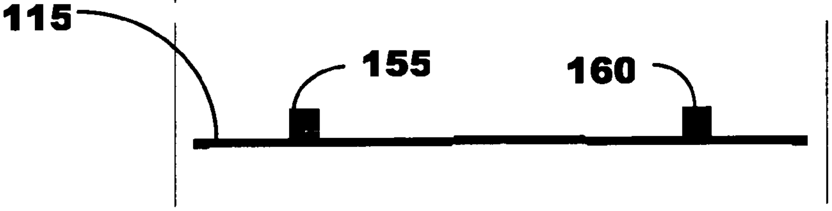
FIG. 10B is a diagram illustrating a cross section of a mass loads positioned along a cMUT membrane.
Figure 11:
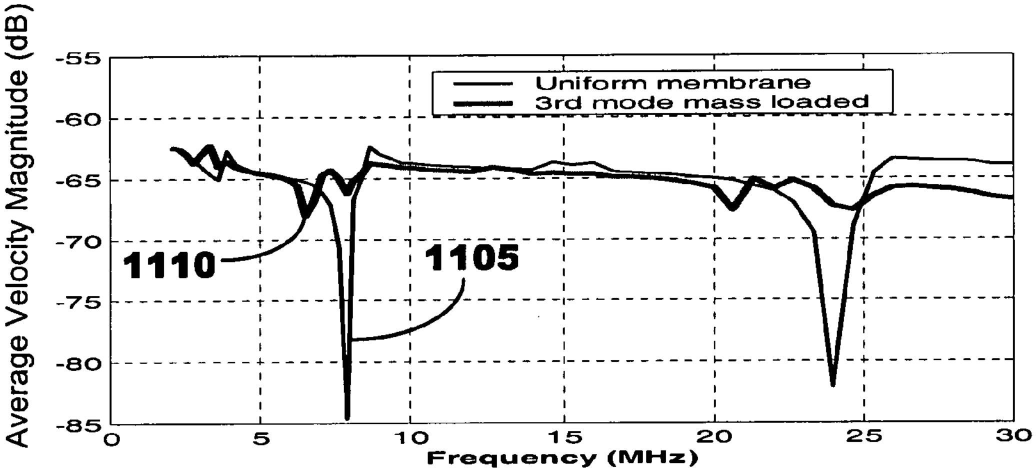
FIG. 11 is a diagram illustrating a comparison of an average velocity for the cMUT membrane illustrated in FIG. 1 being loaded and unloaded with mass loads.

The mass loads are preferably Gold due to its high density and low stiffness. The Gold can be configured to have a thickness of approximately one micro-meter and a width of approximately two micro-meters. The mass loads can be positioned at the peak displacement locations 1015, 1020 as shown in FIG. 10A-B. As shown in FIGS. 10A-B, by positioning the mass loads at peak displacement locations 1015, 1020 the third vibration mode frequency can be shifted from approximately 8 MHz (see 1105) to approximately 6.5 Mhz (see 1110) (FIG. 11). The shifting of a third vibration mode frequency for the membrane can occur without significantly affecting the surrounding vibration modes of the membrane, such as the second and fourth vibration modes.

As an example of the mass loading approach discussed above, the membrane can be designed to reduce a null occurring at approximately 8 MHz in a cMUT spectrum, as shown in FIG. 11. The membrane can be loaded with different mass loads positioned to correspond with a third vibration mode. The mass loads can have a width and thickness of approximately one micro-meter, or a thickness of approximately one micro-meter and a width of approximately two micro-meters. As shown in FIG. 11, positioning the mass loads along the membrane adjusts the average velocity of the membrane.

FIG. 11 shows a reduction on the null 1110 occurring at approximately 8 MHz. Thus, by enhancing the shape or thickness of the membrane, the frequency response of the membrane can be optimized. As further illustrated by FIG. 11, the mass loading does not greatly affect the average velocity of the membrane for most of the spectrum, which evinces that the mass loading of the membrane does not reduce the overall efficiency of the cMUT. The resulting frequency spectrum of the cMUT can be further shaped by continuously positioning additional mass loads along the membrane.

A preferred application utilizing cMUTs with high order vibration mode control as contemplated by the present invention is harmonic imaging. Since mass loads can be used to change the location of peaks in a cMUT's frequency spectrum, signals received at desired frequency ranges can be improved. In addition, by patterning cMUT electrodes into multiple elements, as discussed above, vibrations local to the multiple elements can be selectively detected. For example, a cMUT having a dual electrode element structure having side electrode elements with a width of approximately 10 micro-meters and a center electrode element of approximately 15 micro-meters can be used to selectively detect vibrations occurring at different vibration modes.

Figure 12:
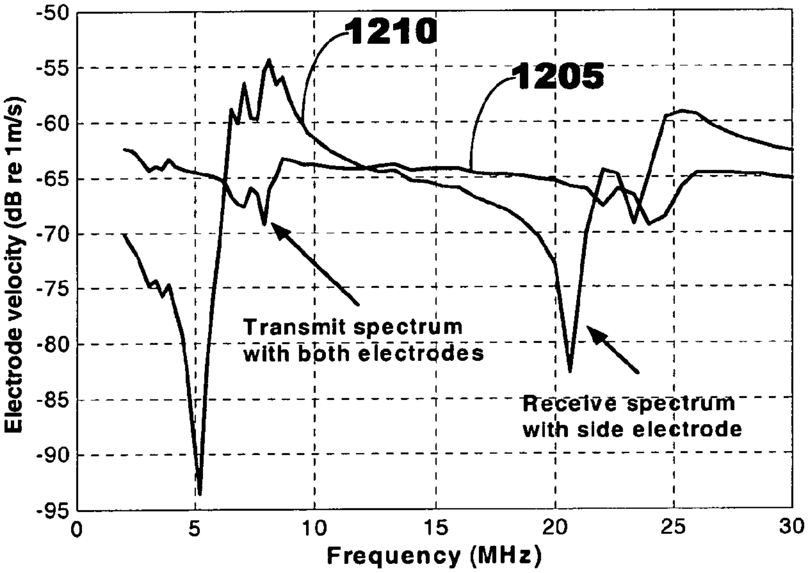
FIG. 12 is a diagram of a sample calculated average velocity corresponding to transmit and receive electrode elements for a harmonic cMUT.

FIG. 12 shows an estimated transmit and receive spectra of a harmonic cMUT. Both center and side electrode elements can be used in transmitting ultrasonic energy, and only side electrode elements can be used to receive ultrasonic energy. As FIG. 12 illustrates, a harmonic cMUT can have a wide-band transmit spectrum 1205 suitable for transmitting a fundamental frequency of approximately 4 MHz. In addition, the spectrum of the received signal 1210, which shows that the harmonic signals around 8 MHz, is amplified relative to the transmitted spectrum by nearly 15 dB. Since harmonic signals are subject to more attenuation, the present invention provides improved cMUT design with enhanced receive and transmit frequency spectrums.

FIGS. 13A and 13B illustrate a cMUT 1300 with an asymmetric membrane 1315 and electrode element 1330 in accordance with a preferred embodiment of the present invention. As shown in FIG. 13, a cMUT 1300 generally comprises a substrate 1305, a membrane 1315, and an electrode element 1330. The membrane 1315 is elongated and the electrode element 1330 can be disposed within the membrane 1315 so that it is suspended above the substrate 1305, as shown in FIG. 13B.

The membrane 1315 can be configured to include a plurality of widths to achieve a plurality of membrane characteristics in a single membrane 1315. It will be understood that the widths of various elements of the cMUT 1300 are shown in FIG. 13A, while the thicknesses of the elements are shown in FIG. 13B. For example, the membrane 1315 can be configured into a generally trapezoidal shape wherein the width of the membrane 1315 at a first end 1320 is smaller than the width of the membrane 1315 at a second end 1325. And although the thickness of the membrane 1315 appears uniform and symmetric in FIG. 13B, it will be understood that it not need be so uniform and symmetric. In a preferred embodiment, the shape of the membrane 1315 is asymmetric about a line of bisection 1350. In some embodiments, the line of bisection can be a lateral line of bisection 1350. The lateral line of bisection 1350 can demarcate a position halfway between the first end 1335 and the second end 1340 of the membrane 1315 as shown in FIG. 13A. The lateral line of bisection 1350 can also demarcate other positions between the first end 1335 and the second end 1340 of the membrane 1315.

The membrane 1315 exhibits non-uniform flex characteristics along its length due to the varied width along the length of the membrane 1315. Assuming uniform materiality, portions of the membrane 1315 having a greater width will flex more easily than portions of the membrane 1315 having a smaller width. The flex characteristics of the membrane 1315 are affected by the material used to fabricate the membrane as well as the length, width, and thickness of the membrane 1315. Assuming uniform materiality, each different width portion of the membrane 1315 vibrates at a different fundamental frequency. Accordingly, by varying the width along the length of the membrane 1315, the membrane 1315 can transmit and receive an ultra-wideband signal.

Due to the non-uniform flex characteristics of the membrane 1315, it may be desirable to use an electrode element 1330 that is adapted to provide a non-uniform capacitive force on the membrane 1330. If a standard symmetric electrode is used, a uniform force is exerted on each portion of the membrane 1315. Accordingly, a first portion of the membrane 1315 could be driven to collapse while another portion of the membrane 1315 is not collapsed. In a preferred embodiment of the present invention, a non-uniform electrode element 1330 is used to apply a non-uniform force along the length of the electrode element 1330 to the membrane 1315, thereby flexing the membrane a substantially equal amount across the length of the membrane 1315. In such an embodiment, multiple portions of the membrane 1315, or even a majority of the membrane 1315, can be driven to collapse simultaneously.

FIG. 13 illustrates the cMUT 1300 having an asymmetric electrode element 1330. And although the thickness of the electrode 1330 appears uniform and symmetric, in FIG. 13B, it will be understood that it need not be so uniform and symmetric. The electrode element 1330 of the cMUT can be appropriately shaped so that the electrical sensitivity of the electrode element 1330 is uniform along the length of the membrane 1315. In a preferred embodiment of the present invention, it is desirable for all parts of the membrane to be biased to approximately 90-95% of the corresponding collapse voltage at a single DC bias level. Also, the electrode element 1330 can be placed such that the membrane 1315 is symmetrically excited in transmission and the symmetric vibration modes are preferably detected.

The electrode element 1330 can be configured to include a plurality of widths to provide a plurality of forces to the membrane 1315. For example, the electrode element 1330 can be configured into a generally trapezoidal shape wherein the width of the electrode element 1330 at a first end 1335 is different than the width of the electrode element 1330 at a second end 1340. In a preferred embodiment, the shape of the membrane 1315 is asymmetric about a line of bisection 1350. The line of bisection 1350 can be a lateral line of bisection 1350 that can demarcate a position halfway between the first end 1335 and the second end 1340 of the electrode element 1330. Alternatively, the lateral line of bisection can demarcate other positions between the first end 1335 and the second end 1340 of the electrode element 1330. The lateral line of bisection of the membrane 1315 need not be equivalent to the lateral line of bisection of the electrode element 1330, although such is shown in FIG. 13A.

As shown in FIG. 13A, the membrane 1315 and the electrode element 1330 can be orientated so that their widths vary inversely. For example, the first end 1335 of the electrode element 1330 can correspond with the first end 1320 of the membrane 1315. Similarly, the second end 1325 of the membrane 1315 can correspond with the second end 1340 of the electrode element 1330. In alternative embodiments, the membrane 1315 and the electrode element 1330 can be orientated in other arrangements, and other factors may affect the orientation of the membrane 1315 and the electrode element 1315. For example, the shape and the orientation of the electrode element 1330 can depend on the thickness of the membrane 1330.

In a preferred embodiment, the second end 1325 of the membrane 1315 can be approximately twenty micro-meters wide, and the membrane can be approximately 0.8 micro-meters thick and made of silicon nitride. The electrode element 1330 can be made of aluminum that is approximately 0.16 micro-meters thick. The electrode element 1330 can be generally disposed in the middle of the silicon nitride membrane 1315. If a gap 1314 that is approximately 0.16 micro-meters separates the membrane 1315 from a bottom electrode proximate the substrate 1305, the membrane 1315 will collapse at around approximately 138 volts DC bias if the second end 1340 of the electrode element 1330 is approximately ten micro-meters wide. Further, if the first end 1320 of the membrane 1315 is approximately twelve micro-meters wide, the first end 1335 of the electrode element can be approximately 7.8 micro-meters wide to have a collapse voltage of approximately 138 volts. With these dimensions, a majority of the membrane 1315, can be driven to collapse substantially simultaneously by applying a single DC bias to the electrode element 1330.

In a preferred embodiment of the present invention, the aspect ratio of the membrane 1315 (average length/average width) is larger than approximately two. In such an embodiment, the dynamics, or resonances, of the membrane 1315 will be dominated by the width dimension. By varying the width of the membrane 1315 over the length dimension, the anti-resonances of the different sections, frequencies at which the average membrane velocity is approximately zero over a cross section, will be distributed over a relatively narrow frequency range, so that the overall uniformity of the frequency response can be centered at a desired level. This approach does not aim to broaden the frequency range by having a broad peak around the first mode of the cMUT. Rather, the ultra-wide bandwidth is achieved by bridging the peaks due to first, second, and third modes with a smoother transition.

Figure 16:
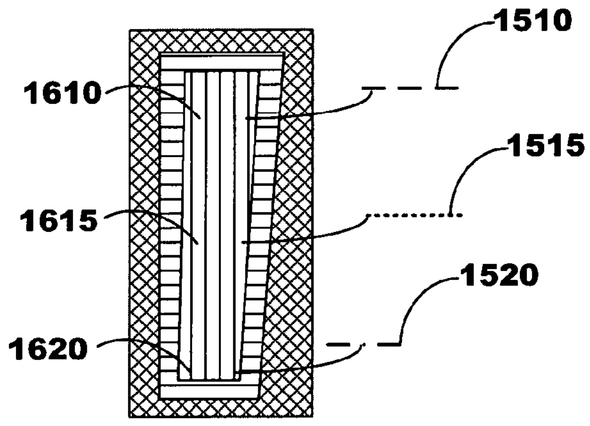
FIG. 16 illustrates a top view of a cMUT having asymmetric properties in accordance with a preferred embodiment of the present invention showing sections of the cMUT membrane having a frequency response that corresponds to the response diagram of FIG. 15.

FIG. 14 illustrates a schematic graph of a pulse echo spectrum of a cMUT array element in accordance with a preferred embodiment of the present invention. The first band 1405 substantially corresponds to the first vibration mode of the membrane 1315, which most resembles a uniform piston motion. The second band 1410 substantially corresponds to the second symmetric mode of the membrane 1315, which has a net average particle velocity over the membrane. The ideal anti-symmetric modes of the membrane 1315 are not excited during transmit assuming that the membrane 1315 and the electrode element 1330 are substantially uniform and symmetric around a central axis of various cross sections of a cMUT as shown in FIG. 16. Also, in the receive mode, a uniform incident pressure wave will not typically generate a net average displacement when the membrane displacement is anti-symmetric. Since in many applications of the present invention, the membrane 1315 is immersed in a water-like medium, the mode shapes may not be exactly the same as the same membrane in vacuum, but can be obtained through a different analysis and experimental techniques.

As shown in FIG. 14, the bands 1405, 1410 can be used separately for ultrasound imaging at two or more different frequency ranges. For example, and not by limitation, the first mode can be used to perform imaging at approximately 12 MHz, and the second mode can be used to perform imaging at approximately 40 MHz. This scheme of operation is generally used in applications where the same cMUT array is used for imaging at two different frequency ranges. Furthermore, the location and bandwidth around these modes can be adjusted using micromachining techniques during the fabrication of cMUT membranes 1315.

Figure 15:
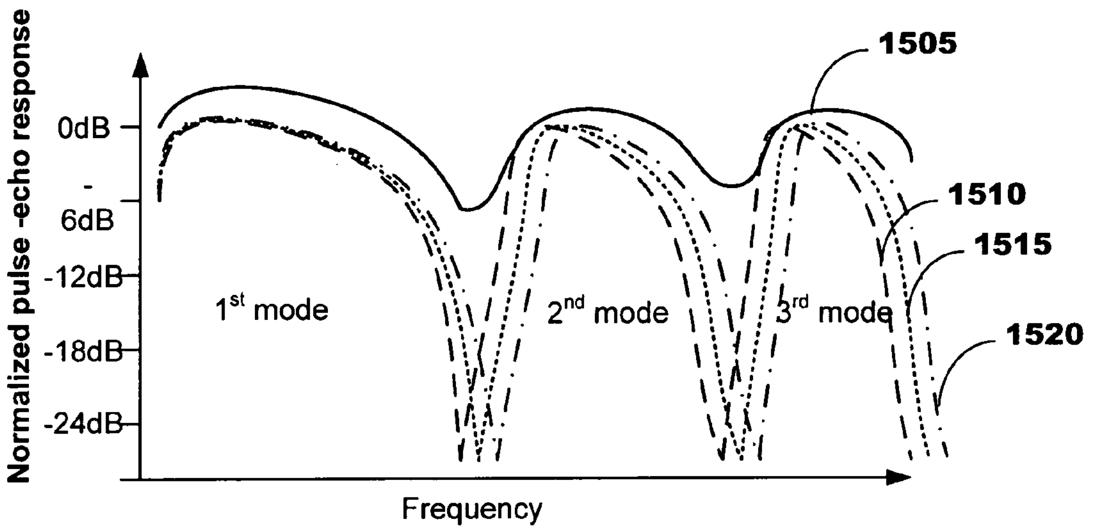
FIG. 15 illustrates a sample pulse-echo frequency spectrum response diagram of a cMUT having asymmetric properties in accordance with a preferred embodiment of the present invention.

For many applications, a transducer that is sensitive over a very broad frequency is desired. In addition, it is not necessary to have sensitivity of the transducer to be uniform in a 6 dB band. In some applications, it is preferable that the variation be below a certain limit, i.e., 12 dB over a frequency range of interest as shown in FIG. 15. Electronic and digital filtering techniques can be used to compensate for limited sensitivity and process the signals for ultra-wide band imaging, harmonic imaging with coded excitation, or harmonic imaging with contrast agents. The cMUT frequency response shown in FIG. 14 is not preferable for these applications because of the deep nulls due to the anti-resonances of the immersed membranes. Since all the membranes constituting the cMUT array element are of uniform in geometry, these nulls are very well defined. This problem can be addressed by taking advantage of microfabrication techniques to fabricate cMUT membranes.

FIG. 15 shows a combined frequency response 1505 that can be achieved through the combination of three frequency responses 1510, 1515, 1520. Typically, only a slight (1-10%) variation of the width over the length of the membrane is suitable to achieve desired results. For other applications, a more severe variation in width is preferable. These frequency responses correspond to certain regions along the cMUT illustrated in FIG. 16.

FIG. 16 illustrates a top view of a cMUT membrane and corresponding regions for producing frequency responses corresponding to the frequency responses illustrated in FIG. 15. As shown, region 1610 produces frequency response 1510, region 1615 produces frequency response 1515, and region 1620 produces frequency response 1520.

Figure 17:
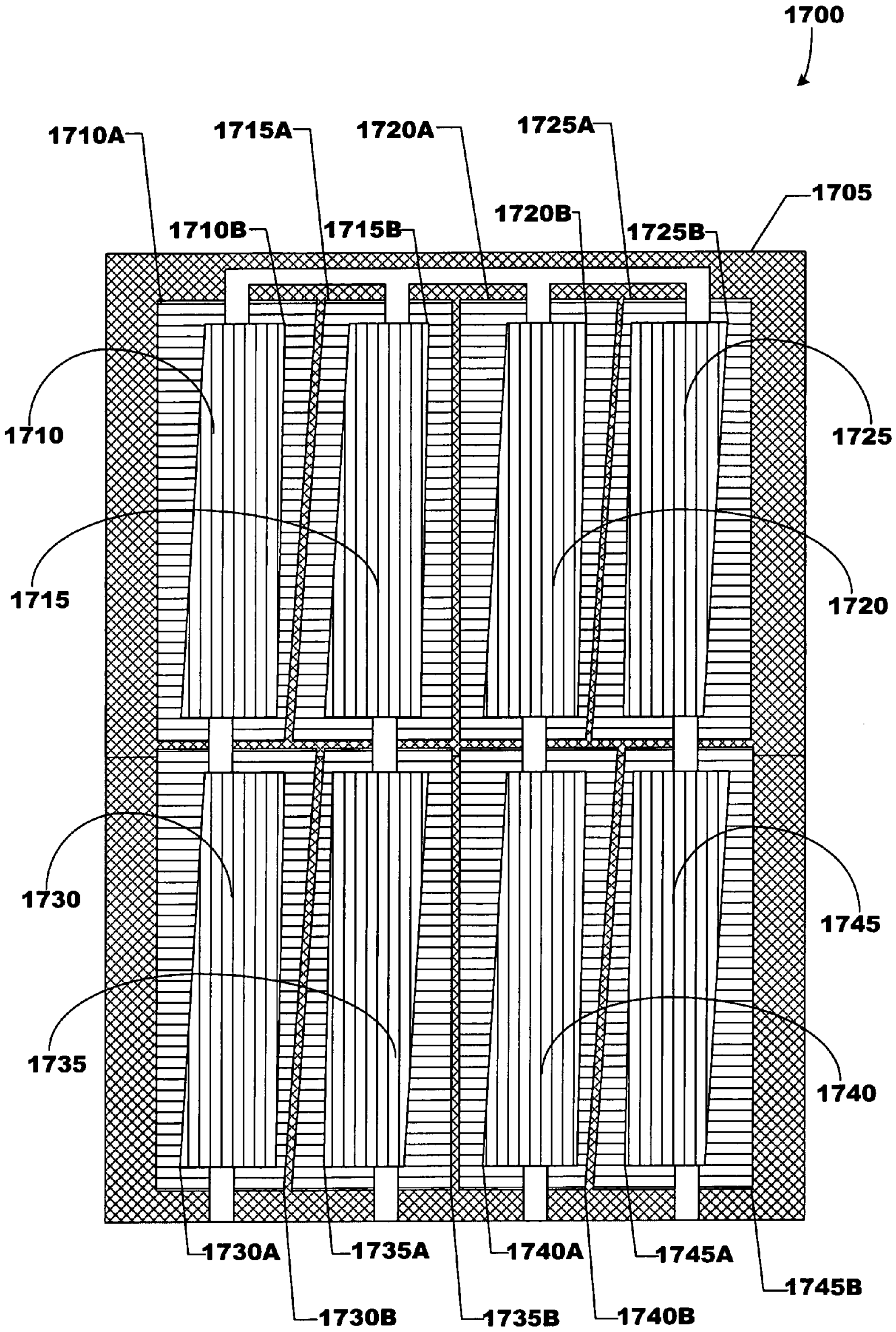
FIG. 17 illustrates a cMUT array element comprised of multiple cMUTs having asymmetric properties in accordance with a preferred embodiment of the present invention.

FIG. 17 shows a plurality of cMUTs, each with a trapezoidal membrane. The plurality of cMUTs are arranged in accordance with a preferred embodiment of the present invention. As shown in FIG. 17, the plurality of cMUTs 1710, 1715, 1720, 1725, 1730, 1735, 1740, 1745 can be arranged on a single substrate 1705. Each of the cMUTs 1710, 1715, 1720, 1725, 1730, 1735, 1740, 1745 has a membrane (indicated by A) and an electrode element (indicated by B). For example, the cMUT 1720 has a membrane 1720A and an electrode element 1720B. This and similar configurations can be used to maximize the active (vibrating) surface area over a transducer array element. Additionally, multiple cMUTs of the plurality of cMUTs can be electrically combined by coupling the electrode elements to form a cMUT or a cMUT element array.

As shown in FIG. 17, the cMUTs can be orientated on the substrate 1705 such that the membranes alternate in direction such that a wide end of a membrane is proximate a narrow end of another membrane. For example, the wider end of the membrane 1740B is located proximate the shorter width end of the membrane 1745B. Such orientation enables multiple cMUTs having asymmetric properties to be arranged an a single substrate 1705.

In an alternative embodiment of the present invention, similar frequency equalization and center frequency adjustments of the frequency bands can be achieved by changing the membrane geometry in the thickness dimension. FIG. 18A shows a top view of a cMUT 1800 with a shaped mass load in accordance with a preferred embodiment of the present invention. The cMUT 1800 generally comprises a substrate 1805, a membrane 1810, and an electrode 1825. In addition, the cMUT 1800 can include a cavity 1809 defined by the membrane 1810 as shown in FIGS. 18B and 18C. The electrode 1825 can be disposed within the membrane 1810, and is shown as a dashed line box in FIG. 18A. The membrane 1810 can have a first end 1810A and a second end 1810B. The first end 1810A can have a width greater than the second end 1810B.

The cMUT 1800 can also include mass loads 1815, 1820. The mass loads 1815, 1820 can have varied widths across their lengths. For example, the mass load 1815 can have a first end 1815A and a second end 1815B, and the first end 1815A can have a width greater than the second end 1815B. Likewise, the mass load 1820 can have a first end 1820A and a second end 1820B, and the first end 1820A can have a width greater than the second end 1820B. The mass loads 1815, 1820 can be portions of the membrane 1810 or can be disposed proximate the membrane 1810.

FIGS. 18B and 18C show cross-section views of the cMUT 1800 illustrating the various widths of the mass loads taken at lines A-A and B-B. As is evident by comparing the width of mass loads 1815, 1820 in FIGS. 18B and 18C, the mass loads 1815, 1820 have a greater width in FIG. 18B than in FIG. 18C.

By shaping the ends 1810A, 1810B of the membrane 1810, the center frequency of the modes of the membrane 1810 can be moved to desired locations. The mass loads 1820, 1825 can also be used to locate the vibration modes of the membrane 1810 at desired center frequencies, such as harmonics. Furthermore, by changing the width of the mass loads 1820, 1825 over their length dimensions, the frequency response can be similar to that of trapezoidal membranes. The vibration shapes of the first and higher modes of the membrane 1810 can be controlled by the mass distribution on the membrane 1810. In addition, the electrode element 1825 location can be optimized to maximize reception of a signal for a particular mode.

FIGS. 19A and 19B illustrate cross-section views of a uniform cMUT membrane (FIG. 19A) and a multi-mode optimized cMUT membrane (FIG. 19B). In addition, these figures illustrate sample vibration mode diagrams corresponding to the cMUTs. As shown in FIG. 19A, a first mode displacement profile 1950 and a second mode displacement profile 1955 correspond to the uniform cMUT membrane shown in FIG. 19A. Also, as shown in FIG. 19B, a first mode displacement profile 1850 and a second mode displacement profile 1855 correspond to the multi-mode optimized cMUT membrane shown in FIG. 19B.

The displacement profiles 1955, 1855 illustrate that the optimized cMUT membrane 1810 (FIG. 19B) with mass loads 1815, 1820 has an improved second mode displacement profile 1855 for as compared to the second mode displacement profile 1955 of the cMUT membrane 1910 (FIG. 19A). The displacement profile is enhanced because the mode displacement for the second mode corresponds with the electrode element 1825 enabling enhanced reception and transmission of signals.

While the various embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all applicable equivalents.

I claim:

1. A cMUT comprising:

a membrane having a length, a width, and a uniform thickness;

wherein the membrane is asymmetric about a line of bisection across the length of the membrane.

2. The cMUT of claim 1, the membrane further having a first end and a second end, wherein the width of the membrane at the first end is greater than the width of the membrane at the second end, and wherein the distance from the first end to the second end defines the length of the membrane.

3. The cMUT of claim 1, wherein the membrane requires a first collapse force to drive the membrane to a collapse state at a first point proximate the first end and a second collapse force to drive the membrane to a collapse state at a second point proximate the second end, and wherein the first collapse force is lower than the second collapse force.

4. The cMUT of claim 1, further comprising:

an electrode element having a length defined as the distance between a first end and a second end;

wherein the electrode element is asymmetric about a line of bisection across the length of the electrode element.

5. The cMUT of claim 3, further comprising:

an electrode element having a length and a width, the length defined as the distance between a first end and a second end;

wherein the width of the electrode element at the first end is less than the width of the electrode element at the second end.

6. The cMUT of claim 5, wherein the electrode element is adapted to provide the first collapse force and the second collapse force, flexing the membrane at the first point and the second point a substantially equal amount.

7. The cMUT of claim 1, wherein the membrane width varies across the length of the membrane such that the membrane has a plurality of cross sections, wherein each cross section of the plurality of cross sections has a different width, and wherein each cross section of the plurality of cross sections has a different fundamental frequency.

8. The cMUT of claim 2, wherein the length of the membrane is greater than two times the width of the membrane at the first end.

9. The cMUT of claim 1, further comprising an electrode element having a length and a width, the length defined as the distance between a first end and a second end, wherein the width of the electrode element at the first end is less than the width of the electrode element at the second end, and wherein the electrode element is adapted to provide a first collapse force and a second collapse force, flexing the membrane at the first point and the second point a substantially equal amount; and wherein the membrane has a vibration mode and wherein the width of the membrane is adapted to alter the vibration mode of the membrane and the flexing characteristics of the membrane.

10. The cMUT of claim 1, wherein the membrane is adapted to transmit and receive ultra-wideband signals.

11. The cMUT of claim 1, wherein the membrane is substantially trapezoidal.

12. A cMUT comprising:

a substrate and a membrane;

one or more mass loads proximate the membrane and configured to modify vibration characteristics of the membrane, the one or more mass loads having a varied width across their length such that mass distribution of the one or more mass loads is non-uniform; and an electrode disposed within the membrane or on the substrate at a position to maximize reception of an ultrasonic signal for a predetermined vibration mode.

13. The cMUT of claim 12, wherein the one or more mass loads are formed as part of the membrane such that the membrane has a non-uniform mass load across its length and width.

14. The cMUT of claim 12, wherein the one or more mass loads comprises a first mass load and a second mass load set off from each other and located on respective halves of the membrane, the first and second mass loads having a length substantially equal to the membrane and having widths tapered along the lengths of the first and second mass loads.

15. The cMUT of claim 12, wherein the electrode is asymmetric about a line of bisection across the length of the electrode.

16. The cMUT of claim 12, wherein the electrode is configured to transmit and receive ultra-wideband signals.

17. The cMUT of claim 12, wherein the one or more mass loads are positioned relative to the position of the electrode partially based on vibration characteristics of the membrane.

18. The cMUT of claim 12, wherein the one or more mass loads are formed of a malleable non-rigid material.

19. The cMUT of claim 12, the membrane is asymmetric about a line of bisection across its length.

20. The cMUT of claim 12, the membrane has substantially trapezoidal shape.

21. A cMUT comprising:

a membrane that is asymmetric about a line of bisection across the length of the membrane;

one or more mass loads proximate the membrane and configured to modify vibration characteristics of the membrane; and one or more electrodes disposed within the membrane or on the substrate, the one or more electrodes configured to receive and transmit ultrasonic signals.

22. The cMUT of claim 21, having two mass loads as the one or more mass loads and having a single electrode as the one or more electrodes, wherein the two mass loads are shaped and sized to have a varied widths across their length and arranged in a symmetric arrangement relative to the electrode.

23. The cMUT of claim 21, having a single mass load as the one or more mass loads and having a single electrode as the one or more electrodes, wherein the mass load is shaped and sized to have a varied width across its length and arranged in a symmetric arrangement relative to the electrode.

24. The cMUT of claim 21, wherein the membrane is arranged to have a width that varies inversely relative to the one or more electrodes.

25. The cMUT of claim 21, wherein the one or more electrodes form electrode elements operatively configured to transmit or receive an ultrasonic wave separately from each other.

26. The cMUT of claim 21, wherein the one or more electrodes have varying widths relative to their lengths.

* * * * *